United States Patent [19]

Builder et al.

[11] Patent Number: 5,451,660

[45] Date of Patent: Sep. 19, 1995

[54] METHOD FOR PURIFYING POLYPEPTIDES

[75] Inventors: Stuart E. Builder, Belmont; Charles V. Olson, Pacifica; David Reifsnyder, San Mateo, all of Calif.

[73] Assignee: Genentech, Inc., South San Francisco, Calif.

[21] Appl. No.: 166,337

[22] Filed: Dec. 13, 1993

[51] Int. Cl.⁶ .................... A61K 38/18; A61K 38/30; C07K 1/22; C07K 14/475

[52] U.S. Cl. .................... 530/344; 530/399; 530/413; 530/300; 530/350; 530/351; 530/324; 514/21

[58] Field of Search .............. 530/344, 392, 399, 412, 530/413, 417, 420, 422, 424, 300, 350, 351, 324, 303, 305, 397, 398; 514/8, 12, 21

[56] References Cited

U.S. PATENT DOCUMENTS

| | | | |
|---|---|---|---|
| 3,869,482 | 3/1975 | Wolfe | 554/83 |
| 3,876,775 | 4/1975 | Izaka et al. | 514/21 |
| 3,904,751 | 9/1975 | Zwisler et al. | 530/381 |
| 4,199,450 | 4/1980 | Dulout et al. | 210/656 |
| 4,652,529 | 3/1987 | Collins et al. | 436/92 |
| 4,677,192 | 6/1987 | Obermeier et al. | 530/305 |
| 4,725,673 | 2/1988 | Herring | 530/381 |
| 4,732,683 | 3/1988 | Georgiades et al. | 210/635 |
| 4,738,926 | 4/1988 | Hamada et al. | 435/239 |
| 4,777,242 | 10/1988 | Nelles | 530/381 |
| 4,849,434 | 7/1989 | Enomoto et al. | 514/342 |
| 4,894,330 | 1/1990 | Hershenson et al. | 435/69.51 |
| 4,902,783 | 2/1990 | Goda et al. | 530/415 |
| 4,908,432 | 3/1990 | Yip | 530/351 |
| 5,004,688 | 4/1991 | Craig et al. | 435/69.3 |
| 5,028,531 | 7/1991 | Ueder et al. | 435/69.4 |
| 5,057,426 | 10/1991 | Henco et al. | 435/270 |
| 5,071,959 | 12/1991 | Capron et al. | 530/351 |
| 5,084,384 | 1/1992 | Wong et al. | 435/69.4 |
| 5,158,875 | 10/1992 | Miller et al. | 435/69.1 |
| 5,231,178 | 7/1993 | Holtz et al. | 530/399 |
| 5,278,284 | 1/1994 | Lusk et al. | 530/305 |

FOREIGN PATENT DOCUMENTS

| | | | |
|---|---|---|---|
| 0304161 | 2/1989 | European Pat. Off. | 530/417 |
| 337492 | 10/1989 | European Pat. Off. | |
| 431679 | 6/1991 | European Pat. Off. | |
| 2653034 | 4/1991 | France | |
| 209187 | 4/1984 | German Dem. Rep. | |
| 217823 | 1/1985 | German Dem. Rep. | |
| 280174 | 6/1990 | German Dem. Rep. | |
| 286721 | 2/1991 | German Dem. Rep. | |
| 298275 | 2/1992 | German Dem. Rep. | |
| 295872 | 11/1991 | Germany | 530/344 |
| 73-008482 | 3/1973 | Japan | |
| 73-019318 | 6/1973 | Japan | |
| 50-116691 | 9/1975 | Japan | |
| 51-118810 | 10/1976 | Japan | |
| 59-159753 | 9/1984 | Japan | |
| 64-51097 | 2/1989 | Japan | |
| 2-234692 | 9/1990 | Japan | |
| 9000748 | 2/1990 | Rep. of Korea | |
| 9206401 | 8/1992 | Rep. of Korea | |

(List continued on next page.)

OTHER PUBLICATIONS

Horvath—High Performance Liquid Chromatography vol. I 76–80 1980.

Horvath—High Performance Liquid Chromatography vol. 2, 124–127 & 131–134 1980.

Heftman "Chromatography" Part A A139–A140 &

(List continued on next page.)

*Primary Examiner*—Michael G. Wityshyn
*Assistant Examiner*—Nancy J. Gromet
*Attorney, Agent, or Firm*—Janet E. Hasak

[57] ABSTRACT

A process is provided for selectively separating a polypeptide of interest from components of differing hydrophobicity in a mixture comprising the steps of:

(a) passing the mixture through underivatized silica particles such that the polypeptide adheres to the silica particles;

(b) washing the silica particles to remove impurities; and (c) eluting the polypeptide from the silica particles with a buffer comprising an alcoholic or polar aprotic solvent and an alkaline earth, an alkali metal, or an inorganic ammonium salt.

25 Claims, 10 Drawing Sheets

FIG. 10

FOREIGN PATENT DOCUMENTS 9208377   9/1992   Rep. of Korea .
9208378   9/1992   Rep. of Korea .
187815   12/1981   Switzerland .
243336    5/1987   Switzerland .
560614    7/1977   U.S.S.R. .
1272227  11/1986   U.S.S.R. .
WO93/00361 1/1993  WIPO .

OTHER PUBLICATIONS

A166–A167 1983.

Stock et al. "Chromatographic Methods" 26–32 & 37–38 1974.

Adachi et al., "Effects of Differences in Charge and Hydrophobicity of Surface Amino Acids of Hemoglobins on High-Performance Gel-Permeation Chromatography", *J. Chromatogr.*, 428:247–254 (1988).

Anspach et al., "Comparative Study of Zorbax Bio Series FG 250 and GF 450 and TSK-Gel 3000 SW and SWXL Columns in Size-Exclusion Chromatography of Proteins", *J. Chromatog.*, 443:45–54 (1988).

Bock et al., "Protein Purification: Adsorption Chromatography on Controlled Pore Glass with the Use of Chaotropic Buffers", *Science*, 191:380–383 (1976).

Byrne et al., "Procedure for isolation of Gangliosides in High Yield and Purity: Simultaneous Isolation of Neutral Glycosphingolipids", *Analytical Biochem.*, 148:163–173 (1985).

Chadha et al., "Chromatography of Human Leukocyte Interferon on Controlled Pore Glass", *Prep. Biochem.*, 11:467–482 (1981).

Chadha et al., "Adsorption of Human Alpha (Leukocyte) Interferon on Glass: Contributions of Electrostatic and Hydrophobic Forces", *J. Interferon Re.*, 2:229–234 (1982).

Cornell et al., "Isolation of Insulin-Like Growth Factors I and II from Human Plasma", *Prep. Biochem.*, 14:123–138 (1984).

Duhamel et al., "Isomerisation Oxaziridine-Amide Sur Gel De Silice Obtention Non Classique D'Une Liaison Peptidique", *Tetrahedron Lett.*, 26:6065–6066 (1985).

Edy et al., "Purifcation of Interferon by Adsorption Chromatography on Controlled Pore Glass", *J. Gen. Virol.*, 33:517–521 (1976).

Flouret et al., "Synthesis of Oxytocin Using Iodine for Oxidative Cyclization and Silica Gel Adsorption Chromatography for Purification", *Int. J. Pept. Protein Res.*, 13:137–141 (1979).

Hemmasi et al., "Synthesis of the C-terminal Undeca- -and Protected Docosapeptide of Bovine Insulin B-Chain", *Hoppe-Seyler's Z. Physiol Chem.*, 365:485–492 (1984).

Hillar et al., "Small Peptides Bound to Polysomal RNA Inhibit Gene Expression in Cell-Free Systems, Replication of Stimulated Lymphocytes and DNA Repair in Isolated Chromatin", *Physiol. Chem. Phys. Med. NMR*, 17:307–323 (1985).

Hillar et al., "Nuclear Peptides from Calf Liver: Large Scale Isolation and Fractionation; Control of Gene Expression in Cell-Free Systems, and Inhibition of Growth of Cells in Culture" *Physiol. Chem. Phys. Med. NMR*, 17:325–343 (1985).

Hillar et al., "Nuclear Peptides from Calf Liver: Large Scale Isolation and Fractionation: Control of Gene Expression in Cell-Free-Systems, and Inhibition of Growth of Cells in Culture", *Bas. Appl. Histochem.*, 31:299–313 (1987).

Huennekens et al., "Transport of Folate Compounds into Mammalian and Bacterial Cells", *Chemistry and Biology of Pteridines*, ed. by Pfleidever (Berlin, de Gruyter, 1975), pp. 179–196.

Jentsch et al., "Bee Venom Peptides XVIII Peptide-M and MCD-Peptide: Isolation and Characterization", *Int. J. Pept. Protein Res.*, 9:78–79 (1977).

Kiselev et al., "Molecular Sieve Chromatography of Polymers and Proteins on Macroporous Silica Gels", in *Column Chromatography*, 5th Int. Symposium (Lausanne 7–10 Oct. 1969) pp. 124–125.

Loginova et al., *Priki, Biokhim, Mikrobiol.*, 14:715–718 (1978) (Abstract in English).

Lu et al., *Shengwu Huazue Yu Shengwu Wuli Jinzhan 48:4648 (1982).*

Manning et al., "Reversed-Phase Liquid Chromatography of Elastin Peptides", *J. Chromatog.*, 487:41–50 (1989).

Mizutani, "Adsorption Chromatography of Biopolymers on Porous Glass", *J. Lig. Chromatog.*, 8:925–983 (1985).

Mizutani, "Decreased Activity of Proteins Adsorbed onto Glass Surfaces with Porous Glass as a Reference":, *J. Pharm. Sci.*, 69:279–280 (1980).

(List continued on next page.)

OTHER PUBLICATIONS

Mizutani, "Adsorption of Antibody and Globulin onto Glass Surfaces", *J. Pharm. Sci.*, 69:1226–1227 (1980).

Mizutani et al., "Comparison of Elution Patterns of Proteins Chromatographed on Controlled-Pore Glass and CarboxymethylCellulose", *J. Chrom.* 168:143–150 (1979).

Moks et al., "Large-Scale Affinity Purification of Human Insulin-Like Growth Factor I from Culture Medium of *Escherichia Coli*" *Bio/Technology*, 5:379–382 (1987).

Mordarski et al., "Antibiotics Produced By Streptomyces Olivaceus 142.II. Isolation, Purification and Activity Spectrum of Antibiotic WR 142-FPG", *Archivum Immunologiae et Therapiae Experimentalis*, 25:273–283, (1977).

Morise et al., "Biological Activity of Partially Purified Digitalis-like Substance and Na-K-ATPase Inhibitor in Rats", *Japanese Circulation Journal*, 52:1309–1316 (1988).

Mount et al., "Purification and Characterization of Epidermal Growth Factor ($\beta$-Urogastrone) and Epidermal Growth Factor Fragments from Large Volumes of Human Urine", *Archives of Biochem. and Biophys.*, 240(1):32–42, (1985).

Pan et al., "Structural Characterization of Human Interferon Y", *Eur. J. Biochem.*, 166:145–149, (1987).

Pickart et al., "Purification of Growth-Promoting Peptides and Proteins, and of Histones, By High Pressure Silica Gel Chromatography", *Preparative Biochemistry*, 5(5 & 6):397–412, (1975).

Pillot et al., "Immunochemical Structure of the Hepatitis B Surface Antigen Vaccine-I. Treatment of Immobilized HBsAg By Dissociation Agents with or without Enzymatic Digestion and Identification of Polypeptides By Protein Blotting", *Molec. Immun.* 21(1):53–60, (1984).

Schall et al., "Human Macrophage Inflammatory Protein $\sigma$ (MIP-1$\sigma$) and MIP-1$\beta$ Chemokines Attract Distinct Populations of Lymphocytes", *J. Exp. Med.*, 177:1821–1825, (1993).

Schmidt et al., "High Performance Liquid Chromatography of Proteins on a Diol-Bonded Silica Gel Stationary Phase", *Anal. Chem.*, 52:177–182, (1980).

Singhalj et al., "Presence of Fucolipid Antigens with Mono-and Dimeric X Determinant (Le$^x$) in the Circulating Immune Complexes of Patients with Adenocarcinoma", *Cancer Res.*, 47:5566–5571, (1987).

Skogen et al., "Endogenous Digoxin-like Immunocreative Factors Eliminated from Serum Samples by Hydrophobic Silica-Gel Extraction and Enzyme Immunoassay", *Clin. Chem.*, 33/3:401–404, (1987).

Sofer, "Current Applications of Chromatography in Biotechnology", *Bio/Tech.*, 4:712–715, (1986).

Stankovic et al., "Purification of Gramicidin A", *Anal., Biochem.*, 184:100–103, (1990).

Stoffel et al., "The Primary Structure of Bovine Brain Myelin Lipophilin (Proteolipid Apoprotein)", *Hoppe-Seyler's Z. Physiol Chem.*, 364:1455–1466, (1983).

Sulkowski, "Purification of Porteins by IMAC", *Trends in Biotechnology*, 3:1–7 (1985).

Takagi et al., "Effect of Salt Concentration on the Elution Properties of Complexes Formed Between Sodium Dodecylsulphate and Protein Polypeptides in High-Performance Silica Gel Chromatography", *J. of Chroma.*, 208:201–208, (1981).

Tao et al., "Isolation and Characterization of Human Urinary Colony-Stimulating Factor", *Bio. Chem. Hoppe-Seyler*, 368:187–194, (1987).

Trucksess et al., "Extraction, Cleanup, and Quantitative Determination of Aflatoxins $B_1$ and $M_1$ in Beef Liver", *J. Assoc. Off. Anal. Chem.*, 62(5):1080–1082, (1979).

Visser, et al., "Some Bitter Peptides From Rennet—Treated Casein. A Method for Their Purification, Utilizing Chromatographic Separation on Silica Gel", *Neth. Milk Dairy, J.*, 29:319–334, (1975).

Wang et al., "Site of Attachment of 11-cis-Retinal in Bovine Rhodopsin", *Biochemistry*, 19:5111–5117, (1980).

Wang (Qinwei) et al., "The Study of Porous Silica Gel for Aqueous Size Exclusion Chromatographic Use", Kao Teng Hsueh Hsia Hua Hsueh Hsueh Pao, *Chemical Journal of Chinese Universities*, 6:557–561, (1985) (Abstract in English).

Whitman et al., "Purification of Human Lymphoblastoid Cell-Derived Interferon-Alpha by Controlled-Pore Glass Bead Adsorption Chromatography and Molecular Sieving", *J. of Interferon Res.*, 1(2):305–313, (1981).

Yip et al., "Partial Purification and Characterization of Human Y (immune) Interferon", *Proc. Natl. Acad. Sci, U.S.A.*, 78(3):1601–1605, (1981).

METHOD FOR PURIFYING POLYPEPTIDES

BACKGROUND OF THE INVENTION

1. Field of the Invention

This invention relates to a general method for purification of polypeptides of moderate hydrophobicity to substantial homogeneity from a mixture such as a cell culture fluid in a single step.

2. Description of Background and Related Art

The large-scale, economic purification of proteins is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge. Usually, the separation procedure is multi-step, requiring expensive apparatus and chromatography media. For review articles on this subject, see Ogez et al., *Biotech. Adv.*, 7: 467–488 (1989) and Sofer, *Bio/Technology*, 4: 712–715 (1986).

Procedures for purification of proteins from cell debris initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells in the course of the protein production run.

Once a clarified solution containing the protein of interest has been obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. Affinity chromatography, which exploits a specific interaction between the protein to be purified and a second protein (such as a specific antibody), may also be an option for some proteins.

The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through."

For some of these purification techniques, high-pressure liquid chromatography (HPLC) can be performed at preparative scale, allowing a high degree of separation using resins that would require prohibitive column sizes and extremely slow separation steps under more conventional conditions. However, this technique also requires expensive equipment and the use of chromatography columns and packings having the chemical and mechanical stability to permit hundreds or thousands of repeated purifications under high pressure.

Adsorption chromatography has been frequently used in the purification of small molecules such as steroids, and is now finding increasing use for large-scale protein purification. The ability of silica particles to adsorb protein with high capacity and affinity has been known for a long time. The major advance has been the determination of methods for desorption of proteins in high yield and in an active form.

In earlier applications of the method, elution was carried out with pH shifts [Edy et al., *J. Gen. Virol.*, 33: 517–521 (1976)] or chaotropic salts. Whitman et al., *J. Interferon Res.*, 1: 305–312 (1981). Chadha and Sulkowski, *J. Interferon Res.*, 2: 229–234 (1982) introduced alkyl amines and organic solvents as eluants and achieved high recoveries of interferon. They have proposed a theory of mechanisms involved in the binding and desorption of proteins on glass. Chadha and Sulkowski, *Prep. Biochem.*, 11: 467–482 (1981). The theory takes into account both the polar and non-polar forces involved in bonding proteins to silica, and describes the properties that a good eluant must possess to break both types of bonds.

Although many of the experiments have been carried out with "controlled-pore" glass, other porous glasses such as ordinary silica particles can give equivalent performance at a fraction of the cost. Bare silica, which is underivatized silica particles, is primarily sold as a desiccation agent. Silica is a popular backbone for the production of chromatography media, since it is inexpensive and is sufficiently chemically active to accept the addition of a wide range of substituent groups. See Anspach et al., *J. Chromatog.*, 443: 45–54 (1988), where various size-exclusion chromatography columns were examined in eluting protein, and ionic strength of the eluent was changed by varying the salt (sodium chloride) concentration of the phosphate buffer, so as to affect the elution volume of proteins differently for two different columns. In addition, silica particles are robust, allowing repeated use of a column of derivatized silica for purification, and give good solvent flow through the column. Underivatized silica is not generally used as a chromatography medium, although it is used as a filter to remove cellular debris and highly hydrophobic impurities.

Silica particles are available in a variety of forms, with different sizes of particle and pore size within the particle. The size of particle chiefly determines the packing properties of the material, which determine the rate of flow and the back pressure when the material is used as a column. The pore size, however, determines the size of protein that has access to the interior of the pore. Kiselev et al., in *Column Chromatography*, 5th Int. Symposium (Lausanne, 7–10 Oct. 1969), pp. 124–125, have shown that pore sizes of about 500 Å are optimum for the separation of polystyrene molecules in the molecular weight range of 10,000 to 100,000 daltons.

It is known to use silica particles for adsorption of proteins such as interferon-gamma. For example, Pan et al., *Eur. J. Biochem.*, 166: 145–149 (1987) discloses elution with 0.5M TMAC/TrisHCl, pH 8.0. Stankovic et al., *Anal. Biochem.*, 184: 100–103 (1990) employs silica particles to elute gramicidin A with chloroform:methanol (1:1). Manning et al., *J. Chromatog.*, 487: 41–50 (1989) reports use of derivatized silica for separating elastin peptides using methanol and iso-propanol. Skogen et al., *Clin. Chem.*, 33: 401–404 (1987) discloses use of hydrophobic bonded-phase silica particles to extract digoxin-like immunoreactive factors, which are eluted with methanol/water. Byrne et al., *Anal. Biochem.*, 148: 163–173 (1985) discloses isolation of gangliosides with consecutive chromatographies, including silica particles. Takagi et al., *J. Chromatog.*, 208: 201–208 (1981) discloses the effect of salt concentration on the elution properties of complexes formed between sodium dodecyl sulphate and protein polypeptides in high-performance silica particle chromatography. Hillar et al., *Bas. Appl. Histochem.*, 31: 299–313 (1987) uses a silica particle step with a methanol gradient in 0.1M ammonium acetate buffer on a C18 silica particle column to elute nuclear peptides from calf liver. See also Hillar et al., *Physiol. Chem. Phys. Med. NMR*, 17: 325–343 (1985) and Hillar et al., *Physiol. Chem. Phys. Med. NMR*, 17: 307–323 (1985), on purification using this solvent and butan-1-ol-propan-2-ol-acetic acid-water.

Mordarski et al., *Archivum Immunologiae et Therapiae Exper.*, 25: 273 (1977) disclose purification of antibiotics on silica particles using 10% acetone in benzene and then methanol. Jentsch and Muecke, *Int. J. Pept. Protein Res.*, 9: 78–79 (1977) disclose purifying bee venom peptides by chromatography on silica particles equilibrated with butanol-1-pyridine-acetic acid-water. Flouret et al., *Int. J. Pept. Protein Res.*, 13: 137–141 (1979) purify oxytocin by adsorption chromatography on a silica particle column with a combination of methanol and chloroform. Stoffel et al., *Hoppe-Seyler's Z. Physiol. Chem.*, 364: 1455–1466 (1983) purify proteolipid apoprotein by silica particle exclusion chromatography using 90% formic acid as solvent. Hemmasi et al., *Hoppe-Seyler's Z. Physiol. Chem.*, 365: 485–492 (1984) discloses purification of peptide III (decosapeptide of bovine insulin B-chain) on silica particles and Sephadex LH-20 in chloroform: methanol ethylacetate/acetic acid. Trucksess and Stoloff, *J. Assoc. Off. Anal. Chem.*, 62: 1080–1082 (1979) teaches purification of aflatoxin B1 and M1 on a silica particle column, washing with chloroform, and eluting with chloroform-methanol.

See also Visser et al., *Neth. Milk Dairy J.*, 29: 319–334 (1975); Loginova et al., *Prikl. Biokhim. Mikrobiol.*, 14: 715–718 (1978); Schmidt et al., *Anal. Chem.*, 52: 177–182 (1980); Lu et al., *Shengwu Huazue Yu Shengwu Wuli Jinzhan*, 48: 46–48 (1982); Wang et al., *Gaodeng Xuexiao Huaxue Xuebao*, 6: 557–561 (1985); Duhamel et al., *Tetrahedron Lett.*, 26: 6065–6066 (1985); Pickart and Thaler, *Prep. Biochem.*, 5: 397–412 (1975); Pillot and Petit, *Mol. Immunol.*, 21: 53–60 (1984); Morise et al., *Jpn Circ J.*, 52: 1309–1316 (1988); Wang et al., *Biochemistry*, 19: 5111–5117 (1980); Adachi et al., *J. Chromatogr.*. 428: 247–254 (1988); Singhal et al., *Cancer Res.*, 47: 5566–5571 (1987); Tao et al., *Biol. Chem. Hoppe Seyler*, 368: 187–194 (1987); Mount et al., *Arch. Biochem. Biophys.*, 240: 33–42 (1985); and Huennekens and Henderson, *Chemistry and Biology of Pteridines*, ed. by Pfleiderer (Berlin, de Gruyter, 1975).

A review of protein purification on porous glass is provided by Mizutani, *J. Lig. Chromatog.*, 8: 925–983 (1985). On page 947, Mizutani states that addition of 5–10% ethanol in a buffer will increase the eluting force of a protein, with no supporting data or further information. Bock et al., *Science*, 191: 380–383 (1976) discloses protein purification by adsorption chromatography on controlled-pore glass using chaotropic buffers. Other references cited in the Mizutani review are MizuEani, *J. Pharm. Sci.*, 69: 279–282 (1980) using 0.1% SDS during elution, Mizutani and Mizutani, *J. Chrom.*, 168: 143–150 (1979) comparing elution of controlled-pore glass with CM-cellulose using standard proteins, Mizutani, *J. Pharm. Sci.*, 69: 1226–1227 (1980) eluting antibodies from controlled-pore glass using 0.2M glycine (pH 8–9) and 0.1% SDS, and Yip et al., *Proc. Natl. Acad. Sci. USA*, 78: 1601–1605 (1981) eluting interferon-gamma with a combination of sodium chloride and ethylene glycol in phosphate buffer.

Additionally, in the U.S. patent literature, purification of proteins and other molecules using a silica particle absorbent is described by U.S. Pat. Nos. 4,908,432 issued Mar. 13, 1990; U.S. Pat. No. 5,057,426 issued Oct. 15, 1991; U.S. Pat. No. 4,777,242 issued Oct. 11, 1988 (adsorption of tumor necrosis factor onto silica glass beads, washing with buffer solution, and eluting with an aqueous lower alkanol, polyol, amine, or aminoalcohol at pH 8–11); U.S. Pat. No. 5,004,688 issued Apr. 2, 1991; U.S. Pat. No. 4,849,434 issued Jul. 18, 1989; U.S. Pat. No. 5,071,959 issued Dec. 10, 1991; U.S. Pat. No. 4,652,529 issued Mar. 24, 1987; U.S. Pat. No. 4,738,926 issued Apr. 19, 1988; U.S. Pat. No. 4,894,330 issued Jan. 16, 1990; U.S. Pat. No. 4,199,450 issued Apr. 22, 1980; U.S. Pat. No. 3,869,482 issued Mar. 4, 1975; U.S. Pat. No. 3,904,751 issued Sep. 9, 1975; U.S. Pat. No. 4,725,673 issued Feb. 16, 1988; and U.S. Pat. No. 3,876,775 issued Apr. 8, 1975.

Foreign published patent literature on the subject includes JP 1051097 published Feb. 27, 1989; JP 59159753 published Sep. 10, 1984; DD 209,187 published Apr. 25, 1984; EP 431,679 published Jun. 12, 1991; EP 337,492 published Oct. 18, 1989; DD 286,721 published Feb. 7, 1991; JP 90234692 published Sep. 17, 1990; DD 280,174 published Jun. 27, 1990; JP 51118810 published Oct. 19, 1976; JP 73008482 filed as JP 7063138 on Jul. 20, 1970; JP 50116691 published Sep. 12, 1975; JP 73019318 filed as JP 7033355 on Apr. 17, 1970; DD 217,823 published Jan. 23, 1985; DD 298,275 published Feb. 13, 1992; FR 2,653,034 published Apr. 19, 1991; SU 560,614 published Jul. 20, 1977; SU 1,272,227 published Nov. 23, 1986; CS 187,815 published Dec. 15, 1981; CS 243,336 published May 15, 1987; FR 2,600,341 issued Dec. 24, 1987; KR 9206401 published Aug. 6, 1992; WO 93/00361 published Jan. 7, 1993; and KR 9000748 published Feb. 15, 1990.

Chadha and Sulkowski, *Prep. Biochem.*, supra, pioneered the use of tetramethyl ammonium chloride (TMAC) to elute proteins, specifically interferon-alpha, from controlled pore glass. They disclose that partial recovery of interferon-alpha was obtained with 50–75% ethylene glycol, 1M ammonium chloride, or 1M Tris-HCl. However, these reagents were not as selective as TMAC since they also eluted other proteins. See also Pan et al., supra. Even elution with TMAC has several disadvantages. For example, TMAC elutes several other proteins that are relatively hydrophobic compared to the protein insulin-like growth factor (IGF-I), which are difficult to remove from IGF-I in later steps.

IGF-I has been purified using gel filtration followed by ion-exchange on a sulfopropyl-substituted cation-exchange column, followed by buffer exchange and fractionation by a second gel filtration step. Next, preparative isoelectric focusing further separated the IGF-I from impurities with similar isoelectric points, followed by two reverse-phase chromatography steps to obtain pure IGF-I. Cornell et al., *Prep. Biochem.*, 14:123 (1984). Clearly, because of the large number of steps involved, this protocol is relatively inefficient.

An alternative protocol for purifying IGF-I requires the fusion of Protein A to IGF-I by a linker, where the culture supernatant is passed through an affinity column consisting of IgG coupled to agarose. The IGF-I fusion product binds to the column while impurities pass through and the bound material is eluted, treated to remove the linker, and passed through IgG-agarose to remove the free Protein A. See Moks et al., *Bio/Technology*, 5: 379–382 (1987); Sofer, *Bio/Technology*, 4: 712–715 (1986).

IGF-I has been also purified by a series of adsorption-desorption steps employing a combination of cation-exchange and hydrophobic-interaction adsorbents. See U.S. Pat. No. 5,231,178 issued Jul. 27, 1993. Another method for purifying IGF-I involves centrifuging a human IGF-I-containing culture broth, diluting the supernatant with distilled water and adjusting the resulting solution to pH 5.6, passing the solution through a weak anion-exchange resin and 10 mM phosphate buffer solution (pH 5.6), dissolving the human IGF-I fraction in a 150–200 mM NaCl solution, and passing the fraction through a DE cation-exchange resin and 10 mM Tris buffer solution to obtain the final product. See KR 9208377 published Sep. 26, 1992. In addition, KR 9208378 published Sep. 26, 1992 discloses purifying IGF-I by passing a IGF-I-containing culture broth through an anion-exchange resin column, washing the column with phosphate buffer and dissolving with sodium-chloride-containing sodium carbonate solution to obtain the IGF-I fraction, passing the fraction through a cation-exchange resin column and concentrating, and passing the concentrated solution through a gel-filtration column to obtain the final product.

It is an object of the present invention to provide a general method of purifying polypeptides from hydrophobic impurities using only inexpensive underivatized silica particles.

It is another object of the present invention to provide a method of selectively eluting polypeptides from underivatized silica particles using a combination of ionic and organic solvents that does not destroy the silica particles.

It is a specific object of the invention to provide a method of purifying IGF-I from fermentation fluid.

These and other objects will become apparent to one of ordinary skill in the art.

SUMMARY OF THE INVENTION

Accordingly, in one aspect the invention herein provides a process for selectively separating a polypeptide of interest from components of differing hydrophobicity in a mixture comprising the steps of:
(a) passing the mixture through underivatized silica particles such that the polypeptide adheres to the silica particles;
(b) washing the silica particles to remove impurities; and
(c) eluting the polypeptide from the silica particles with a buffer comprising an alcoholic or polar aprotic solvent and an alkaline earth, an alkali metal, or an inorganic ammonium salt.

In another aspect, the invention provides a process of purifying IGF-I from a mixture containing it comprising the steps of:
(a) loading the mixture onto a column of underivatized silica particles;
(b) washing the column with a buffer to remove impurities; and
(c) eluting the IGF-I from the column using a buffer at pH of about 5–8 comprising about 5–40% (v/v) of an alcoholic or polar aprotic solvent and about 0.2 to 3M of an alkaline earth, an alkali metal, or an inorganic ammonium salt.

DETAILED DESCRIPTION OF THE PREFERRED EMBODIMENTS

A. Definitions

Figure 1:
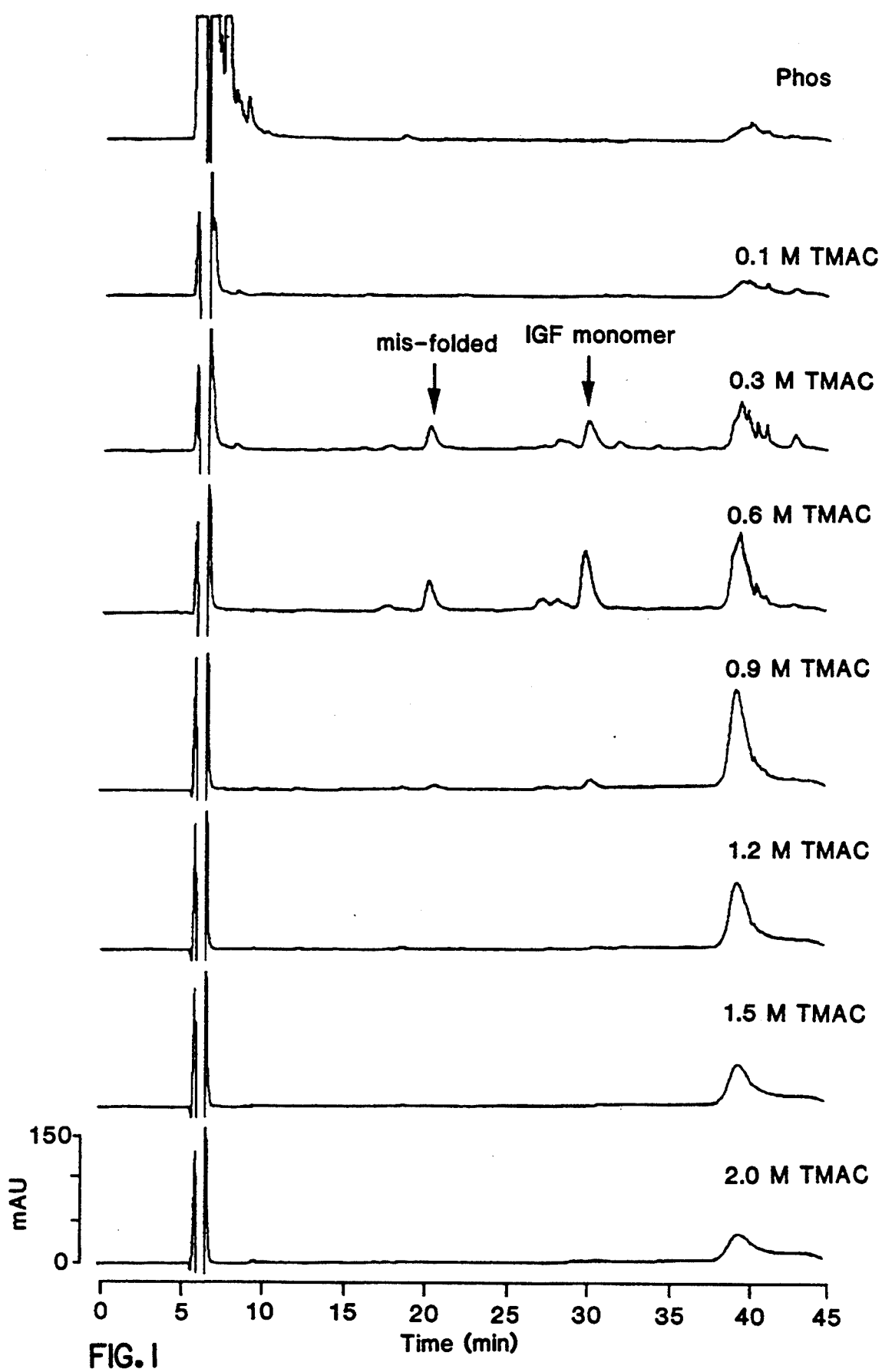
FIG. 1 shows a RP-HPLC analysis of fractions obtained from step increments of TMAC in 0.1M phosphate buffer, pH 7 on silica. The chromatograms in decreasing order from the top are phosphate, 0.1M TMAC, 0.3M TMAC, 0.6M TMAC, 0.9M TMAC, 1.2M TMAC, 1.5M TMAC, and 2.0M TMAC. The arrows on the 0.3M TMAC chromatogram represent mis-folded and IGF monomer (from left to right).

As used herein, "polypeptide of interest" refers generally to peptides and proteins having more than about ten amino acids. The polypeptides may be homologous to the host cell, or preferably, may be exogenous, meaning that they are heterologous, i.e., foreign, to the host cell being utilized, such as a human protein produced by a Chinese hamster ovary cell or by a bacterial cell, or a yeast polypeptide produced by a different yeast or a bacterial or mammalian cell. Preferably, mammalian polypeptides (polypeptides that were originally derived from a mammalian organism) are used, more preferably those which are directly secreted into the medium.

Examples of bacterial polypeptides include, e.g., alkaline phosphatase and $\beta$-lactamase. Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-$\beta$; platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and -II (IGF-I and IGF-II); des(1–3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as; for example, a portion of the AIDS envelope; transport proteins; homing receptors; addressins; regulatory proteins; antibodies; and fragments of any of the above-listed polypeptides.

The preferred polypeptides of interest are those that are easily produced in cells with a minimum of proteolysis and need not be glycosylated for their intended utility. Examples of such mammalian polypeptides include IGF-I, IGF-II, brain IGF-I, growth hormone, relaxin chains, growth hormone releasing factor, insulin chains or pro-insulin, urokinase, immunotoxins, NGF, NT-5, RANTES, MIP-1-alpha, vascular endothelial growth factor, an IGF-I binding protein, a GH binding protein, and antigens. Particularly preferred mammalian polypeptides include IGF-I, brain IGF-I, growth hormone, a neurotrophin such as NGF, NT-3, NT-4, NT-5, and NT-6, including NT-5, an IGF-I binding protein, vascular endothelial growth factor, or RANTES. The most preferred mammalian polypeptide is IGF-I, including full-length IGF-I and brain IGF-I.

As used herein, "IGF-I" refers to insulin-like growth factor-I from any species, including bovine, ovine, porcine, equine, and preferably human, in native sequence or in variant form (such as des-1–3-IGF-I, or brain IGF-I) and recombinantly produced. One method for producing IGF-I is described in EP 128,733 published Dec. 19, 1984.

As used herein, "components of differing hydrophobicity" refers to components contained in the mixture with the polypeptide of interest from which the polypeptide is separated selectively. These components differ in hydrophobicity from the polypeptide of interest.

As used herein, "underivatized silica particles" refers to bare silica beads, also known as silica gel, used in an adsorptive mode such as an adsorptive bed. Bare silica is silica that has free hydroxyl groups, i.e., is not derivatized or modified in any manner, including chemical conjugation or reaction of the hydroxyl groups with any other moiety.

As used herein, "buffer" refers to a buffered solution that resists changes in pH by the action of its acid-base conjugate components.

As used herein, "solvent" refers to alcohols and polar aprotic solvents. Alcohols are meant in the sense of the commonly used terminology for alcohol, preferably alcohols with 1 to 10 carbon atoms, more preferably methanol, ethanol, iso-propanol, n-propanol, or t-butanol, as well as ethylene glycol and polyethylene glycol, and most preferably ethanol or iso-propanol, but excluding propylene glycol and glycerol. Such alcohols are solvents that, when added to aqueous solution, increase the hydrophobicity of the solution by decreasing solution polarity. Polar aprotic solvents include such molecules as, e.g., dimethyl sulfoxide (DMSO), dimethyl formamide (DMF), N-methylpyrrolidone (NMP), tetrahydrofuran (THF), dioxane, acetonitrile, etc., that can be used in place of or in addition to the alcohol. Preferred solvents herein are methanol, ethanol, iso-propanol, n-propanol, or acetonitrile, most preferably ethanol. Excluded from this definition are propylene glycol and glycerol.

As used herein, the phrase "alkaline earth, alkali metal, or inorganic ammonium salt" refers to a salt having a cation from the alkaline earth or alkali metal elements or an ammonium cation and having an inorganic or organic (hydrocarbon-based) anion if the cation is an alkaline earth or alkali metal cation, and having an inorganic anion if the cation is an ammonium cation, i.e., the ammonium is not attached covalently to the anion, as is the case with TMAC. Examples of such salts include sodium chloride, ammonium chloride, sodium citrate, potassium citrate, potassium chloride, magnesium chloride, calcium chloride, sodium phosphate, calcium phosphate, ammonium phosphate, magnesium phosphate, potassium phosphate, sodium sulfate, ammonium sulfate, potassium sulfate, magnesium sulfate, calcium sulfate, etc. Preferred salts herein are chlorides or sulfates. The most preferred salt herein is sodium chloride.

B. Modes for Carrying Out the Invention

In the process of this invention for separating a polypeptide from other components in a mixture, there are three essential steps. In the first, the mixture is passed through the underivatized silica particles such that the polypeptide adheres to those particles. The polypeptide is hence adsorbed onto the silica. While the silica can have any suitable pore size (mean diameter), generally the range of pore size is about 200 to 1500 Å, preferably about 200 to 1000 Å, and more preferably about 225 Å. The particle size of the silica is generally in the range of about 30 to 130 microns. The polypeptide of interest is retained. The other components of the mixture, which are impurities, usually protein or polypeptide impurities, can therefore be easily washed away.

Adsorption of the polypeptide onto the silica particles can be done chromatographically or in a non-chromatographic, batchwise, fashion. Chromatographic adsorption is done by passing the mixture through a bed of silica particles in a column chromatography apparatus. Typically, about one liter of mixture is applied to a column apparatus containing about 50 mL (about 20 g dry weight) of silica particles at a flow rate of about 20 column volumes (CV)/hour.

Non-chromatographic adsorption onto silica is typically done by mixing the mixture with the silica particles in a suitable vessel, e.g., a sealable glass bottle. The preferred method is to add about 300 mL of the silica particles to about one liter of the mixture in a glass bottle and incubate with constant mixing. Adsorption preferably continues for about 1.5 hours at about 4°–8° C., although different times and temperatures are suitable.

In the second step of the process herein, the silica particles are washed to remove impurities. Washing of the silica free of unadsorbed material can also be accomplished without chromatography, or the silica can be poured into a column apparatus, as previously described, for chromatographic adsorption. Batchwise washing is done by draining the mixture from the silica and adding several volumes of a buffer that will not cause the release of the polypeptide of interest adsorbed onto the silica. The preferred buffer has a pH of about 5–8, more preferably a phosphate buffer, and the preferred solvent for washing is an alcohol, as defined above, more preferably ethanol. Most preferably the washing solvent is about 20% (v/v) ethanol in pH 7 phosphate buffer.

Chromatographic washing of the polypeptide-adsorbed silica is done by passing the solvent containing the buffer through the silica at a flow rate of about 10–20 CV/hour until washing is complete, as can be determined by conventional means.

In the third step, the polypeptide of interest is eluted from the washed silica using a buffered solution. The first key ingredient of the buffer is an alcoholic or polar aprotic solvent at a concentration of about 5–40% (v/v), preferably 10–30% (v/v) of the solution, depending, e.g., on the type of polypeptide and solvent. It is most preferably at a concentration of about 20% (v/v).

A second key ingredient of this buffer is an alkaline earth, an alkali metal, or an inorganic ammonium salt, which is present in a concentration of about 0.2 to 3M, preferably 0.5 to 2M, depending mainly on the solvent concentration and the type of alkaline earth, alkali metal, or inorganic ammonium salt and polypeptide employed. For example if the cation is sodium, potassium, or ammonium, the concentration is about 0.5 to 3M, but if the cation is magnesium, the concentration is about 0.2 to 1M. Preferably, the buffer has a pH of about 5 to 8, and most preferably is a phosphate buffer at pH about 7. Most preferably, the solvent is ethanol at a concentration of about 20% (v/v) and the salt is sodium chloride at a concentration of about 1M, in a phosphate buffer at pH 7.

Desorption of the polypeptide of interest can be facilitated at elevated temperatures over a wide range. Desorption at about room temperature is preferred.

Concentration of the eluted polypeptide is usually desired. The preferred method is to concentrate the eluate using an appropriately sized molecular weight cut-off ultrafiltration system. The ultrafiltration retentate can be sterilized by microfiltration or other methods, if desired.

If the polypeptide is made recombinantly, suitable host cells for expressing the DNA encoding the desired polypeptide are the prokaryote, yeast, or higher eukaryotic cells. Suitable prokaryotes for this purpose include bacteria such as archaebacteria and eubacteria. Preferred bacteria are eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*; Bacilli such as *B. subtilis* and *B. licheniformis* (e.g., *B. licheniformis* 41P disclosed in DD 266,710 published Apr. 12, 1989); *Pseudomonas* such as *P. aeruginosa*; *Streptomyces*; *Azotobacter*; *Rhizobia*; *Vitreoscilla*;

and *Paracoccus*. Suitable *E. coli* hosts include *E. coli* W3110 (ATCC 27,325), *E. coli* 294 (ATCC 31,446), *E. coli* B, and *E. coli* X1776 (ATCC 31,537). These examples are illustrative rather than limiting.

Mutant cells of any of the above-mentioned bacteria may also be employed. It is, of course, necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYA177, or pKN410 are used to supply the replicon.

*E. coli* strain W3110 is a preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA$\Delta$; *E. coli* W3110 strain 9E4, which has the complete genotype tonA$\Delta$ ptr3; *E. coli* W3110 strain 27C7 (ATCC 55,244), which has the complete genotype tonA ptr3 phoA$\Delta$E15 $\Delta$ (argF-lac)169 $\Delta$degP $\Delta$ompT kan$^r$; *E. coli* W3110 strain 37D6, which has the complete genotype tonA ptr3 phoA$\Delta$E15 $\Delta$ (argF-lac)169 $\Delta$degP $\Delta$ompT $\Delta$rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990.

In addition to prokaryotes, eukaryotic microbes such as filamentous fungi or yeast are suitable expression hosts for polypeptide-encoding vectors. *Saccharomyces cerevisiae,* or common baker's yeast, is the most commonly used among lower eukaryotic host microorganisms. However, a number of other genera, species, and strains are commonly available and useful herein, such as *Schizosaccharomyces pombe* [Beach and Nurse, *Nature*, 290: 140 (1981); EP 139,383 published May 2, 1985]; *Kluyveromyces* hosts [U.S. Pat. No. 4,943,529; Fleer et al., *Bio/Technology*, 9: 968-975 (1991) ] such as, e.g., *K. lactis* [MW98-8C, CBS683, CBS4574; Louvencourt et al., *J. Bacteriol.*, 737 (1983)], *K. fragilis* (ATCC 12,424), *K. bulgaricus* (ATCC 16,045), *K. wickeramii* (ATCC 24,178), *K. waltii* (ATCC 56,500), *K. drosophilarum* [ATCC 36,906; Van den Berg et al., *Bio/Technology*, 8: 135 (1990)], *K. thermotolerans,* and *K. marxianus; yarrowia* [EP 402,226]; *Pichia pastoris* [EP 183,070; Sreekrishna et al., *J. Basic Microbiol.*, 28: 265-278 (1988) ]; *Candida; Trichoderma reesia* [EP 244,234]; *Neurospora crassa* [Case et al., *Proc. Natl. Acad. Sci. USA*, 76: 5259-5263 (1979)]; *Schwanniomyces* such as *Schwanniomyces occidentalis* [EP 394,538 published Oct. 31, 1990]; and filamentous fungi such as, e.g., *Neurospora, Penicillium, Tolypocladium* [WO 91/00357 published Jan. 10, 1991], and *Aspergillus* hosts such as *A. nidulans* [Ballance et al., *Biochemo Biophys. Res. Commun.*, 112: 284-289 (1983); Tilburn et al., *Gene*, 26: 205-221 (1983); Yelton et al., *Proc. Natl. Acad. Sci. USA*, 81: 1470-1474 (1984)] and *A. niger* [Kelly and Hynes, *EMBO J.*, 4: 475-479 (1985)].

Suitable host cells appropriate for the expression of the DNA encoding the desired polypeptide may also be derived from multicellular organisms. Such host cells are capable of complex processing and glycosylation activities. In principle, any higher eukaryotic cell culture is suitable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6: 47-55 (1988); Miller et al., in *Genetic Engineering,* Setlow, J. K. et al., eds., Vol. 8 (Plenum Publishing, 1986), pp. 277-279; and Maeda et al., *Nature,* 315: 592-594 (1985). A variety of vital strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens,* which has been previously manipulated to contain the DNA encoding the desired polypeptide. During incubation of the plant cell culture with *A. tumefaciens,* the DNA encoding the desired polypeptide is transferred to the plant cell host such that it is transfected, and will, under appropriate conditions, express the DNA encoding the desired polypeptide. In addition, regulatory and signal sequences compatible with plant cells are available, such as the nopaline synthase promoter and polyadenylation signal sequences. Depicker et al., *J. Mol. Appl. Gen.*, 1: 561 (1982). In addition, DNA segments isolated from the upstream region of the T-DNA 780 gene are capable of activating or increasing transcription levels of plant-expressible genes in recombinant DNA-containing plant tissue. EP 321,196 published Jun. 21, 1989.

Examples of useful mammalian host cell lines are monkey kidney CV1 line transformed by SV40 (COS-7, ATCC CRL 1651); human embryonic kidney cell line (293 or 293 cells subcloned for growth in suspension culture); baby hamster kidney cells (BHK, ATCC CCL 10); Chinese hamster ovary cells/-DHFR (CHO); mouse sertoli cells (TM4); monkey kidney cells (CV1, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); TRI cells (Mather et al., *Annals N.Y. Acad. Sci.*, 383: 44-68 [1982]); MRC 5 cells; FS4 cells; and a human hepatoma cell line (Hep G2).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO$_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrahr. Depending on the host cell used, transformation is done using standard techniques appropriate to such cells. The calcium treatment employing calcium chloride, as described in section 1.82 of Sambrook et al., *Molecular Cloning: A Laboratory Manual* [New York: Cold Spring Harbor Laboratory Press, 1989], or electroporation is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published Jun. 29, 1989. In addition, plants may be transformed using ultrasound treatment as described in WO 91/00358 published Jan. 10, 1991.

For mammalian cells without such cell walls, the calcium phosphate precipitation method of Graham and van der Eb, *Virology*, 52: 456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.*, 130: 946 (1977) and Hsiao et al., *Proc. Natl. Acad. Sci.* (USA), 76: 3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* (1990) Vol. 185, pp. 527–537, and Mansour et al., *Nature*, 336: 348–352 (1988).

If prokaryotic cells are used to produce the polypeptide of interest in accordance with the method of this invention, they are cultured in suitable media in which the promoter can be constitutively or artificially induced as described generally, e.g., in Sambrook et al., *Molecular Cloning: A Laboratory Manual* (Cold Spring Harbor Laboratory Press, N.Y. 1989). Examples of suitable media are given below in the example section.

Any necessary supplements besides carbon, nitrogen, and inorganic phosphate sources may also be included at appropriate concentrations introduced alone or as a mixture with another supplement or medium such as a complex nitrogen source. The pH of the medium may be any pH from about 5–9, depending mainly on the host organism.

If mammalian host cells are used to produce the polypeptide of this invention, they may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.*, 58: 44 (1979); Barnes and Sato, *Anal. Biochem.*, 102: 255 (1980); U.S. Pat. Nos. 4,767,704; 4,657,866; 4,927,762; 5,122,469; or 4,560,655; WO 90/03430; WO 87/00195; or U.S. Pat. Re. 30,985, the disclosures of all of which are incorporated herein by reference, may be used as culture media for the host cells. Any of these media may be supplemented as necessary with hormones and/or other growth factors (such as insulin, transfertin, or epidermal growth factor), salts (such as sodium chloride, calcium, magnesium, and phosphate), buffers (such as HEPES); nucleosides (such as adenosine and thymidine), antibiotics (such as Gentamycin ™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of in vitro mammalian cell cultures can be found in *Mammalian Cell Biotechnology: A Practical Approach*, M. Butler, ed. (IRL Press at Oxford University Press, Oxford, 1991).

The above process can be employed whether the polypeptide is intracellular, in the periplasmic space, or directly secreted into the medium. The preferred conditions given herein for isolating a polypeptide are those that allow direct secretion into the medium.

The following procedures are exemplary of suitable purification procedures after the silica step for obtaining even greater purity: fractionation on immunoaffinity or ion-exchange columns; ethanol precipitation; reverse-phase HPLC; hydrophobic interaction chromatography; chromatography on an ion-exchange resin such as S-Sepharose and DEAE; chromatofocusing; SDS-PAGE; ammonium sulfate precipitation; and gel filtration using, for example, Sephadex G-75.

The invention will be more fully understood by reference to the following examples, which are intended to illustrate the invention but not to limit its scope. All literature and patent citations are expressly incorporated by reference.

EXAMPLE I

Recovery of IGF-I from Fermentation Broth

A. Column Preparation

One part of dry silica packing (grade 953 obtained from Davison Chemical Division of W. R. Grace) was resuspended in 5–10 parts of water (twice) to remove fines. A slurry of approximately 1 part resin to 2 parts water was transferred to an appropriately sized glass column. The bed was equilibrated with water until a constant bed length was obtained. Then the top flow adaptor was positioned above the packed bed and the column was equilibrated with water at a flow rate of 20–40 CV/hr. Once a stable baseline was achieved, the column was ready for use. A total of 3 CV of water was generally used to prepare a uniform packed bed. The column dimensions were $1 \times 12.8$ cm (10 mL bed volume). Unless otherwise specified, all of the following steps were conducted at room temperature.

B. Sample Preparation and Loading

The host used to produce recombinant human IGF-I in the fermentation described in this example was a derivative of *E. coli* W3110, designated 27C7. The complete genotype of 27C7 is tonA ptr3 phoAΔE15 Δ (argF-lac) 169 ΔdegP ΔompT kan$^r$ as found in WO 93/11240 published Jun. 10, 1993, the disclosure of which is incorporated herein by reference. Strain 27C7 was deposited on Oct. 30, 1991 in the American Type Culture Collection as ATCC No. 55,244.

The secretion plasmid pLS32Tsc used in this example contains the IGF-I gene. The transcriptional and translational sequences required for expression of the IGF-I gene in *E. coli* are provided by the alkaline phosphatase promoter and the trp Shine-Dalgarno sequence. The lambda $t_o$ transcriptional terminator is situated adjacent to the IGF-I termination codon. Secretion of the protein from the cytoplasm is directed by the lamB signal sequence or alternatively the STII signal sequence. The majority of IGF-I is found in the cell periplasmic space. Plasmid pLS32Tsc confers tetracycline resistance upon the transformed host.

Plasmid pLS32Tsc was constructed in several steps using as intermediate plasmids pLS32, pAPlamB, pLS32lamB, pLS33lamB, and pLS33Tsc as disclosed in detail in WO 93/11240, supra.

Transformants were obtained by standard transformation techniques and selected and purified on LB plates containing 20 mg/L tetracycline. This medium had the following composition: 10 g/L Bacto-Tryptone, 5 g/L yeast extract, 10 g/L sodium chloride, 20 mg/L tetracycline-HCl, and 15 g/L agar.

The fermentation process for producing IGF-I by the direct secretion method using E. coli 27C7/pLS32Tsc was performed in batches ranging from 10 to approximately 1000 liters. A shake flask was prepared by inoculating sterile LB broth containing 20 mg/L tetracycline with freshly thawed stock culture. The shake flask was incubated at 35°–39° C. at 50–200 rpm for 7–12 hours. The shake flask was used to inoculate a secondary inoculum culture grown in a 10-L fermentation vessel using production medium. The secondary inoculum was grown at 35°–39° C. until the optical density at 550 nm reached 20–35. This culture was then used to inoculate the 1000-L production broth. All inocula volumes were between 0.1% and 10% of the initial volume of media.

The composition of the medium is shown below. All medium components were sterilized by heat treatment or filtration.

| Ingredient | Quantity/L |
| --- | --- |
| Glucose* | 10–300 g |
| Ammonium Sulfate | 2–6 g |
| Sodium Phosphate, Monobasic Dihydrate | 1–5 g |
| Potassium Phosphate, Dibasic | 1–5 g |
| Sodium Citrate, Dihydrate | 0.5–5 g |
| Potassium Chloride | 0.5–5 g |
| Magnesium Sulfate, heptahydrate | 0.5–5 g |
| Pluronic Polyol, L61 | 0.1–2 mL |
| Ferric Chloride, Heptahydrate | 10–100 mg |
| Zinc Sulfate, Heptahydrate | 0.1–10 mg |
| Cobalt Chloride, Hexahydrate | 0.1–10 mg |
| Sodium Molybdate, Dihydrate | 0.1–10 mg |
| Cupric Sulfate, Pentahydrate | 0.1–10 mg |
| Boric Acid | 0.1–10 mg |
| Manganese Sulfate, Monohydrate | 0.1–10 mg |
| Tetracycline | 5–30 mg |
| Yeast Extract** | 5–15 g |
| NZ Amine AS** | 5–15 g |
| Methionine** | 0–5 g |
| Ammonium Hydroxide | as required to control pH |
| Sulfuric Acid | as required to comtrol pH |

*A portion of the glucose was added to the medium initially, with the remainder being fed throughout the fermentation.
**These components can be fed throughout the fermentation.

The fermentation process was performed at 35°–39° C. and pH 7.0–7.8. The agitation rate was set at 200–800 rpm and the aeration rate at 0.5–2.0 volumes of air per volume of culture per minute. Production of IGF-I occurred when the phosphate in the medium was depleted. The fermentation was allowed to proceed for 25–35 hours, at which time the culture was chilled prior to harvest. The culture was inactivated by heat treatment using a continuous-flow apparatus with a flow rate of 15–25 L/min at 60°–70° C. or in-tank heat inactivation (10-L scale) at 60°–70° C. for 5–15 minutes. The heat-inactivated culture was centrifuged using a AX Alpha-laval centrifuge or equivalent and then the supernatant was clarified through a depth filter. The clarified fermentation broth was saved for further processing and the cells were discarded.

The clarified broth was loaded directly onto the silica column at a rate of 20–40 CV/hr and a total of 40 CV was loaded. During the load, most of the colored material present in the broth passed through the column as judged by visual inspection. Analysis of the column effluent by HPLC or SDS-PAGE showed that no IGF-I was lost during loading.

C. Wash and Elution with TMAC

After sample loading, the column was washed with 4 CV of 0.01M phosphate, pH 7, until the UV trace returned to baseline. At this point, the packed bed was still a dark brown, indicating that there were appreciable amounts of fermentation components still bound to the column. Then the column was eluted with step increments of TMAC in 0.1M phosphate, pH 7. The rate for the phosphate wash and all subsequent washes was approximately 5 CV/hr. Aliquots from each TMAC wash were analyzed on a 0.46×25 cm Vydac C-18 (5μ/300Å) RP-HPLC column equilibrated with 29% acetonitrile in 0.1% triflouroacetic acid (TFA). IGF-I was eluted with a linear gradient of 29–30% acetonitrile in 0.1% TFA over 30 min. Then the column was regenerated with 60% acetonitrile in 0.1% TFA for 5 min before re-equilibration. A constant flow rate of 0.5 mL/min was used for these analyses and the total time between injections was 45 min. IGF-I monomer, which elutes at approximately 31 min in this assay (FIG. 1), began to elute with 0.3M TMAC. All of the IGF-I was eluted following the 0.9M TMAC step.

Unfortunately, the TMAC elution steps also contained appreciable amounts of undesirable protein impurities that interfered with subsequent purification of IGF-I. A gradient elution was also tried, but this did not improve the purity of IGF-I relative to the protein impurities. Therefore, the effect of different wash steps prior to eluting with TMAC buffer was examined to improve the purity of the silica elution pool.

EXAMPLE II

Effect of NaCl on the Silica Elution

Figure 2:
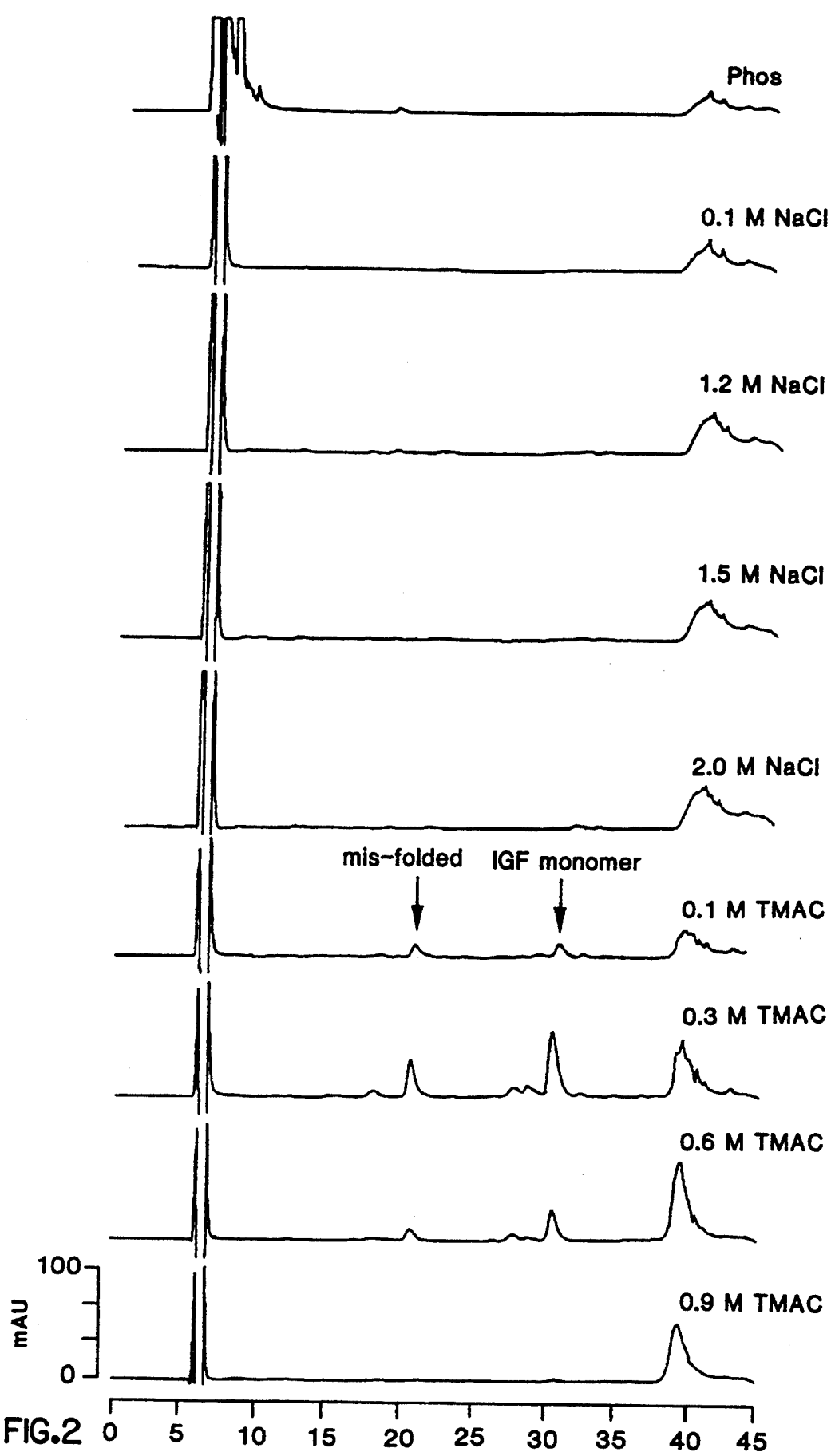
FIG. 2 shows a RP-HPLC analysis of fractions obtained from step increments of NaCl followed by TMAC in 0.1M phosphate buffer, pH 7 on silica. The chromatograms in decreasing order from the top are phosphate, 0.1 NaCl, 1.2M NaCl, 1.5M NaCl, 2.0M NaCl, 0.1M TMAC, 0.3M TMAC, 0.6M TMAC, and 0.9M TMAC. The arrows on the 0.1M TMAC chromatogram represent misfolded and IGF monomer (from left to right).

Silica columns and load conditions were as described in Example I. After washing with 0.1M phosphate buffer, the column was washed with 4-CV increments of buffer containing 0.1–2M NaCl in 0.1M phosphate, pH 7. Then the column was eluted with step increments of TMAC in 0.1M phosphate, pH 7. Results from the HPLC analysis of these fractions as described in Example I are shown in FIG. 2. None of the NaCl increments were effective in eluting IGF-I or in removing any of the impurities prior to TMAC elution. It is significant to note that even 2M NaCl was ineffective in removing any IGF-I or protein impurities, since the conductivity of 2M NaCl buffer exceeds that of the 1M TMAC. Therefore, it is not solely the ionic strength that makes TMAC an effective eluant for proteins bound to silica. Since the elution power of TMAC has been ascribed to its ionic and solvent character, its elution capacity must depend on the interaction of ionic and solvent strength.

EXAMPLE III

Effect of Solvent on the Silica Elution

Figure 3:
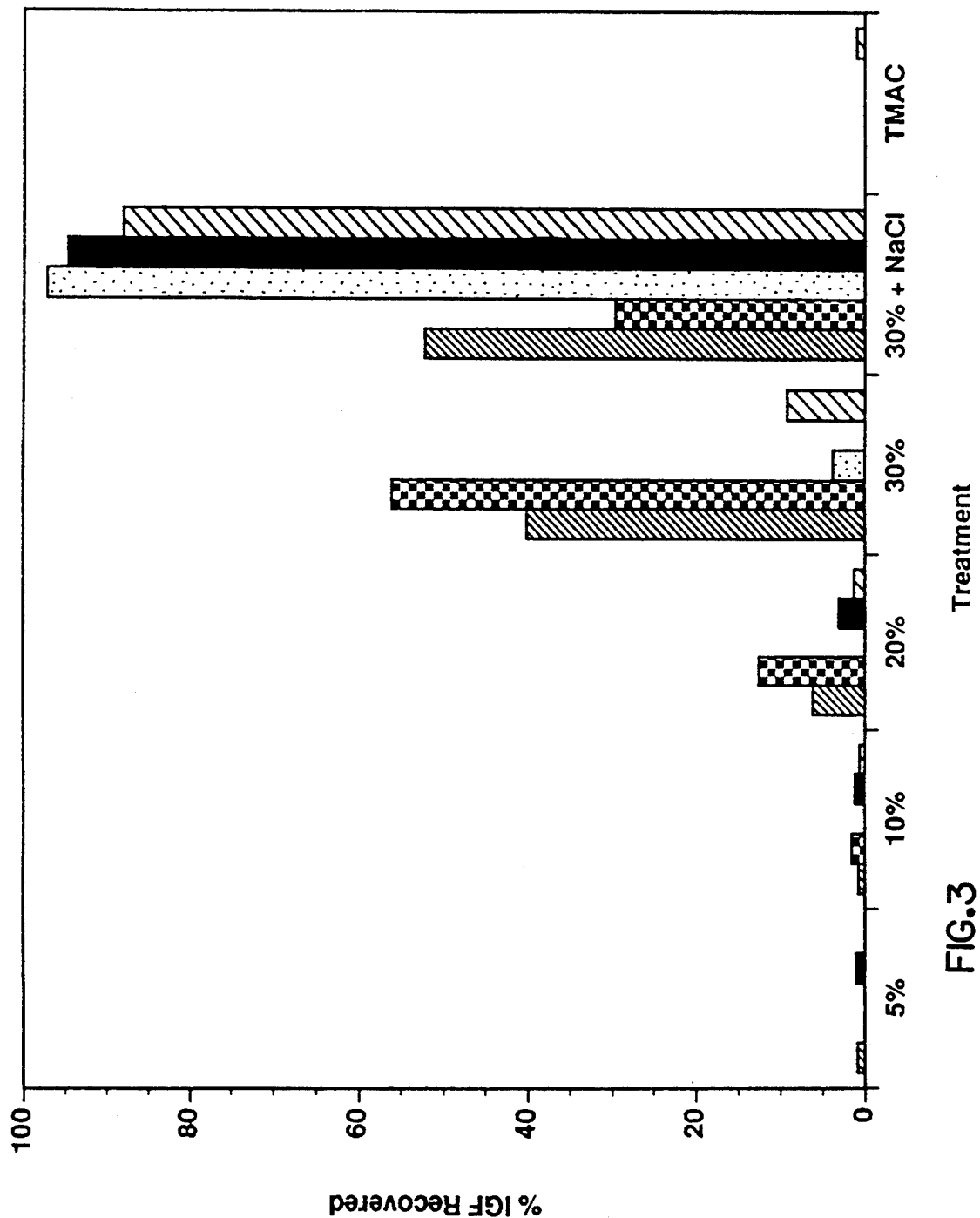
FIG. 3 shows the effect of solvent on IGF-I elution from silica. The closely spaced diagonals are isopropyl alcohol, the checkers are acetonitrile, the dots are methanol, the solid black is ethanol, and the widely spaced diagonals are ethylene glycol.

The effect of various solvents in eluting IGF-I from silica was investigated. For these experiments, the fermentation broth containing IGF-I was loaded onto a silica column as described in Example I. After a wash with 4 CV of 0.1M phosphate, pH 7, the column was washed with 5 bed volumes of solvent at increments of 5, 10, 20, or 30% (v/v) in 0.1M phosphate, pH 7. This was followed by washing with 30% solvent + 1M NaCl to see if there was any benefit in including NaCl to elute IGF-I. Finally, a buffer containing 1M TMAC in 0.1M phosphate, pH 7, was used to see what residual hydrophobic proteins were still on the column after the solvent wash. The solvents tested included: isopropanol, ethylene glycol, methanol, ethanol, acetonitrile, propylene glycol, and glycerol. All samples were analyzed for IGF-I by the RP-HPLC assay as described in Example I. The results from this experiment are summarized in FIG. 3.

In general, all the solvents were effective in eluting IGF-I bound to the silica except propylene glycol and glycerol. No IGF-I was recovered in any wash with these two solvents. The HPLC chromatograms from propylene glycol and glycerol suggested that these solvents interacted with IGF-I, causing it to behave as a much more hydrophobic protein that eluted during the column regeneration step. Therefore, propylene glycol and glycerol were no longer considered as suitable solvents for IGF-I elution from silica.

The elution power of the other solvents could be divided into two groups. Isopropanol and acetonitrile seem to be the stronger eluants, but still required 30% solvent to recover a significant amount of IGF-I. Ethylene glycol, methanol, and ethanol were weaker solvents that required the addition of 1M NaCl to the 30% solvent to elute the bound IGF-I. The addition of NaCl also facilitated IGF-I elution with the stronger solvents, isopropanol and acetonitrile. Investigation of the combination of ethanol and salt having the preferred effect on the elution of IGF-I from silica was continued due to the relative cost, availability, and safety of ethanol relative to the other solvents.

EXAMPLE IV

Effect of Ethanol and NaCl on the Silica Elution

The combination of ethanol and NaCl was investigated using different increments of each component. Three silica columns were prepared and loaded as described in Example I. After loading, each column was washed with 4 CV of 0.1M phosphate, pH 7. Then, columns were washed with 4 CV of phosphate buffer containing either 0.1, 0.6, or 1.5M NaCl+0–30% ethanol (in 5% increments). At the end of the 30% ethanol+NaCl step, the columns were washed with 0.1M phosphate to remove solvent and the column was regenerated with 4 CV of 1M TMAC in 0.1M phosphate, pH 7, to ensure that all of the IGF-I had been eluted.

Figure 4:
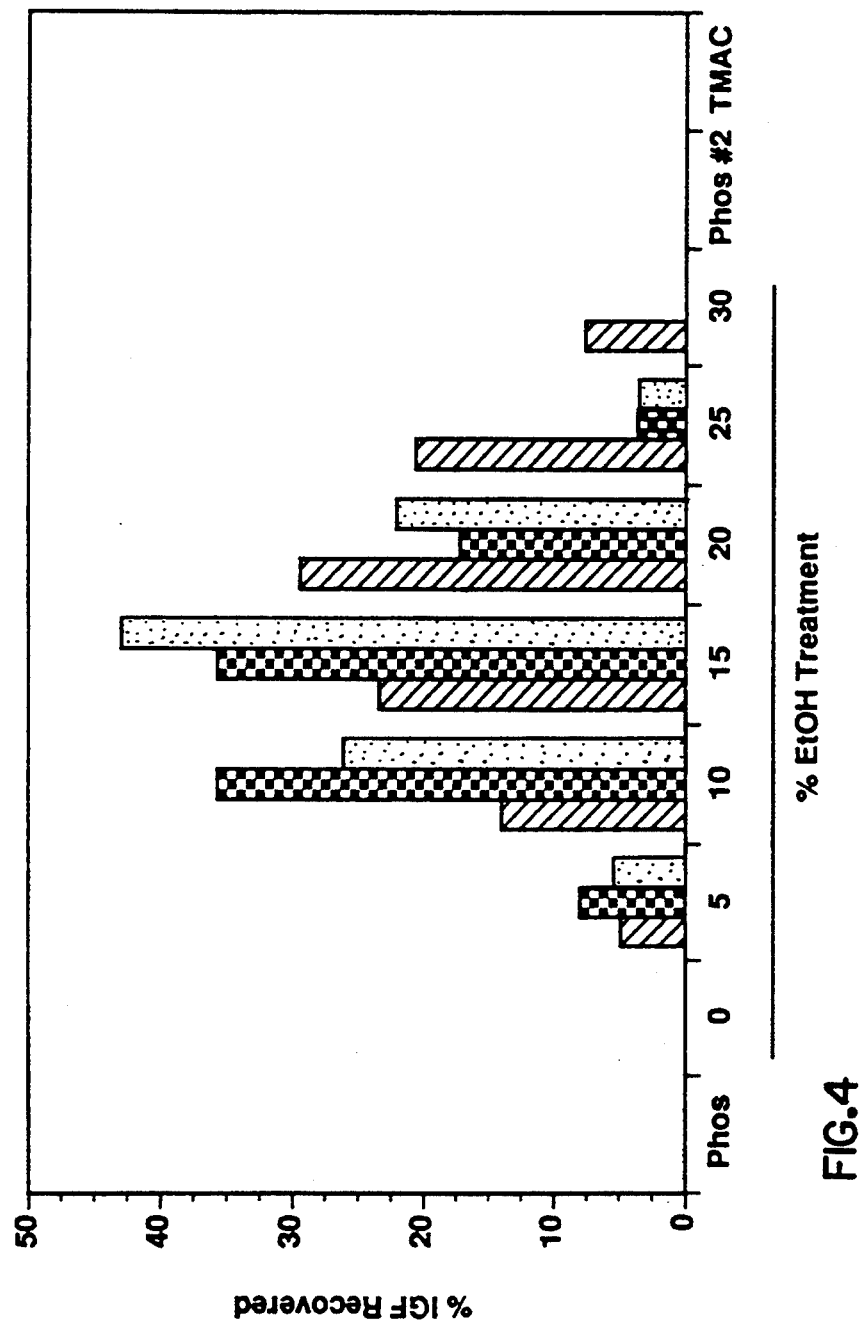
FIG. 4 shows the effect of ethanol and NaCl on IGF-I elution from silica. The diagonals are 0.1M NaCl, the checkers are 0.6M NaCl, and the dots are 1.5M NaCl.

The results from the HPLC analysis of these elutions are shown in FIG. 4. The trends seen with each column are similar. Lower concentrations of NaCl required higher levels of ethanol to remove the IGF-I completely. In fact, there were still appreciable amounts of IGF-I eluted with 0.1M NaCl and 30% ethanol. However, by increasing the level of ethanol, the IGF-I elution profile shifted so that more was obtained at the lower salt concentration. It should also be noted that these levels of NaCl and ethanol were effective in removing all of the IGF-I from the resin, since regenerating the column with TMAC removed no additional IGF-I. The recovery of IGF-I in each treatment was >97% of the total amount loaded to each column. Other experiments in which the amount of ethanol was constant in three columns (10, 20, or 30%) and increments of 0–2M NaCl were investigated gave a similar trend.

EXAMPLE V

Investigation of Preferred Ethanol and NaCl Concentrations for IGF-I Elution Four silica columns were prepared as described in Example I except the packed bed was 5 mL. Clarified fermentation broth containing approximately 10 mg of IGF-I monomer was loaded to each column. After a wash with 4 CV of 0.1M phosphate, pH 7, the columns were washed and eluted with approximately 4 CV of the following components in 0.1M phosphate buffer, pH 7. Prior to the TMAC treatment, each column was washed with approximately 4 CV of 0.1M phosphate, pH 7, to reduce the effect of solvent and NaCl on this regeneration step.

A. 10% ethanol; 10% ethanol+1.5M NaCl; 1M TMAC

B. 0.5M NaCl; 20% ethanol+0.5M NaCl; 1M TMAC

C. 20% ethanol; 20% ethanol+1.0M NaCl; 1M TMAC

D. 1.5M NaCl; 20% ethanol+1.5M NaCl; 1M TMAC

The TMAC wash was included at the end of each combination of ethanol and NaCl to remove any IGF-I bound to the silica after the elution buffer treatment. In addition to removing IGF-I, the TMAC non-specifically eluted many more hydrophobic proteins that were also bound to the silica. Therefore, the TMAC eluate was significantly less pure than the combination of ethanol and NaCl.

Figure 5:
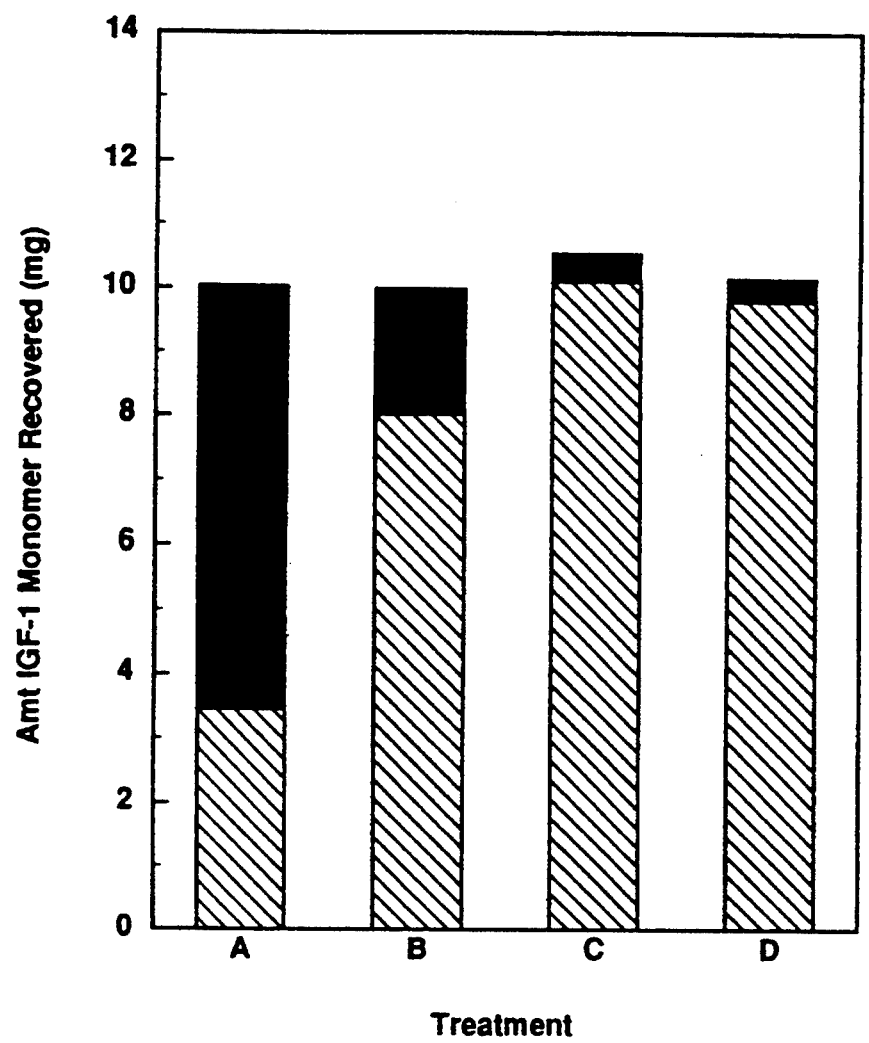
FIG. 5 shows various ethanol and NaCl concentrations for their effect on IGF-I elution from silica, where the solid black portion of the bar is TMAC and the diagonal portion of the bar is ethanol and NaCl. Bar A is 10% ethanol and 1.5M NaCl, Bar B is 20% ethanol and 0.5M NaCl, Bar C is 20% ethanol and 1.0M NaCl, and Bar D is 20% ethanol and 1.5M NaCl.

The results from this experiment are summarized in FIG. 5. In each case, quantitative recovery of IGF-I from all of these conditions was similar (10–10.5 mg). However, the most specific elution of IGF-I was obtained with 20% ethanol and 1 or 1.5M NaCl (conditions C or D). Approximately 95% of the IGF-I monomer was obtained with these conditions. Decreasing the NaCl concentration to 0.5M (B) resulted in incomplete IGF-I elution (80% recovery). However, decreasing ethanol while increasing NaCl had a more drastic effect on IGF-I recovery (A). The wash step prior to elution did not remove IGF-I. However, it did remove varying amounts of hydrophobic impurities. Therefore, the elution pool from 20% ethanol/1M NaCl was slightly purer than that obtained from 1.5M NaCl/20% ethanol. Since the goal of these studies was to obtain the maximum recovery and purity of IGF-I from silica, the most robust elution condition was a combination of 20% ethanol and 1M NaCl. This particular combination was chosen since it gave a safety window in buffer preparation of approximately 5% ethanol and 0.5M NaCl to elute IGF-I bound to silica.

EXAMPLE VI

Comparison of TMAC versus EtOH/NaCl Elution

Figure 6:
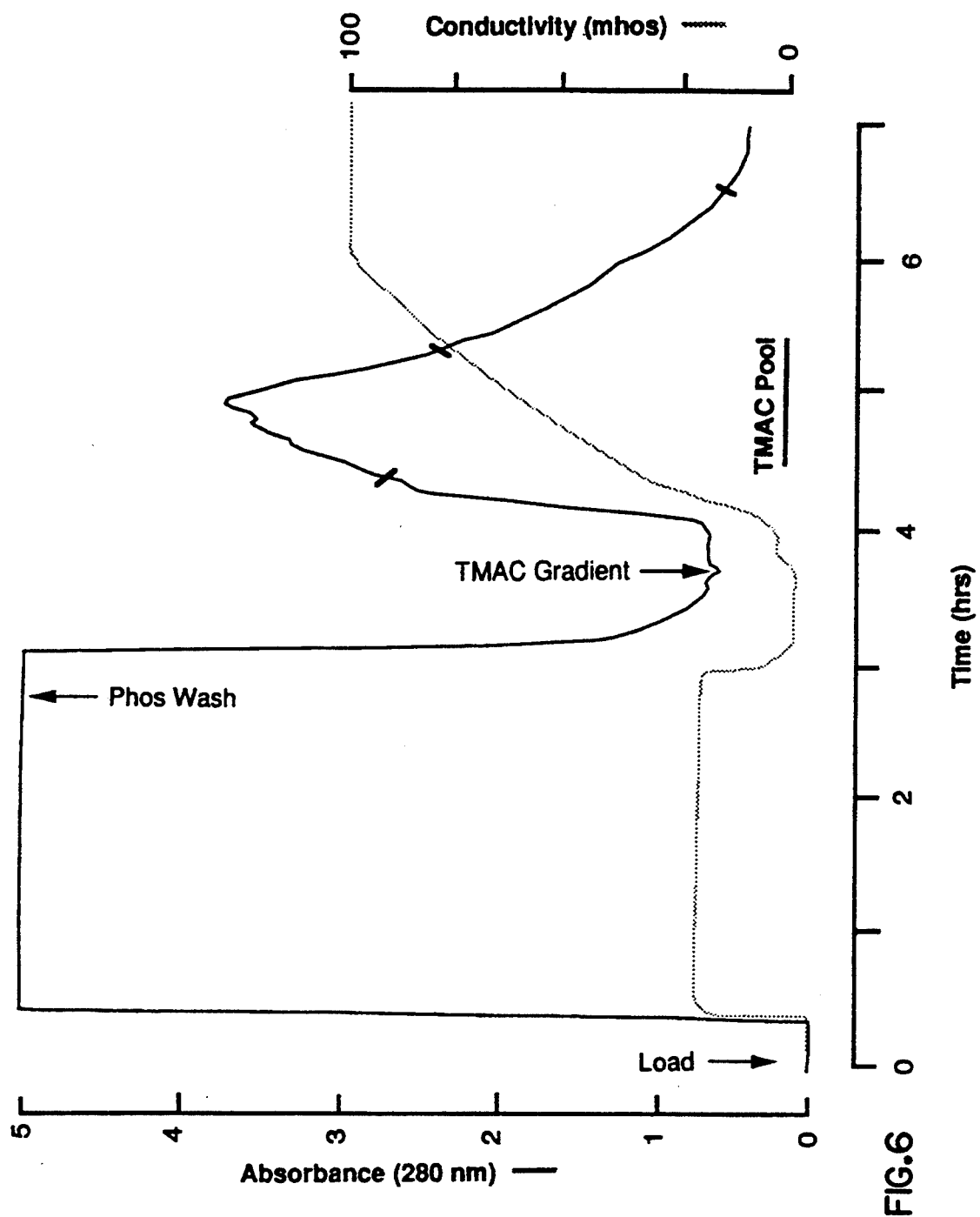
FIG. 6 shows the silica chromatogram using a TMAC gradient to elute bound IGF-I. The solid line is the absorbance (280 nm) and the stippled line is conductivity. Arrows indicate (from left to right): column loading, phosphate wash after loading, and initiation of TMAC gradient. Fractions were collected during elution and assayed for IGF-I by RP-HPLC assay. Fractions containing IGF-I were pooled (TMAC Pool between 4.4 and 5.2 hours). Fractions from 0.7 to 1M TMAC were pooled as indicated from approximately 5.2 to 6.5 hours.
Figure 7:
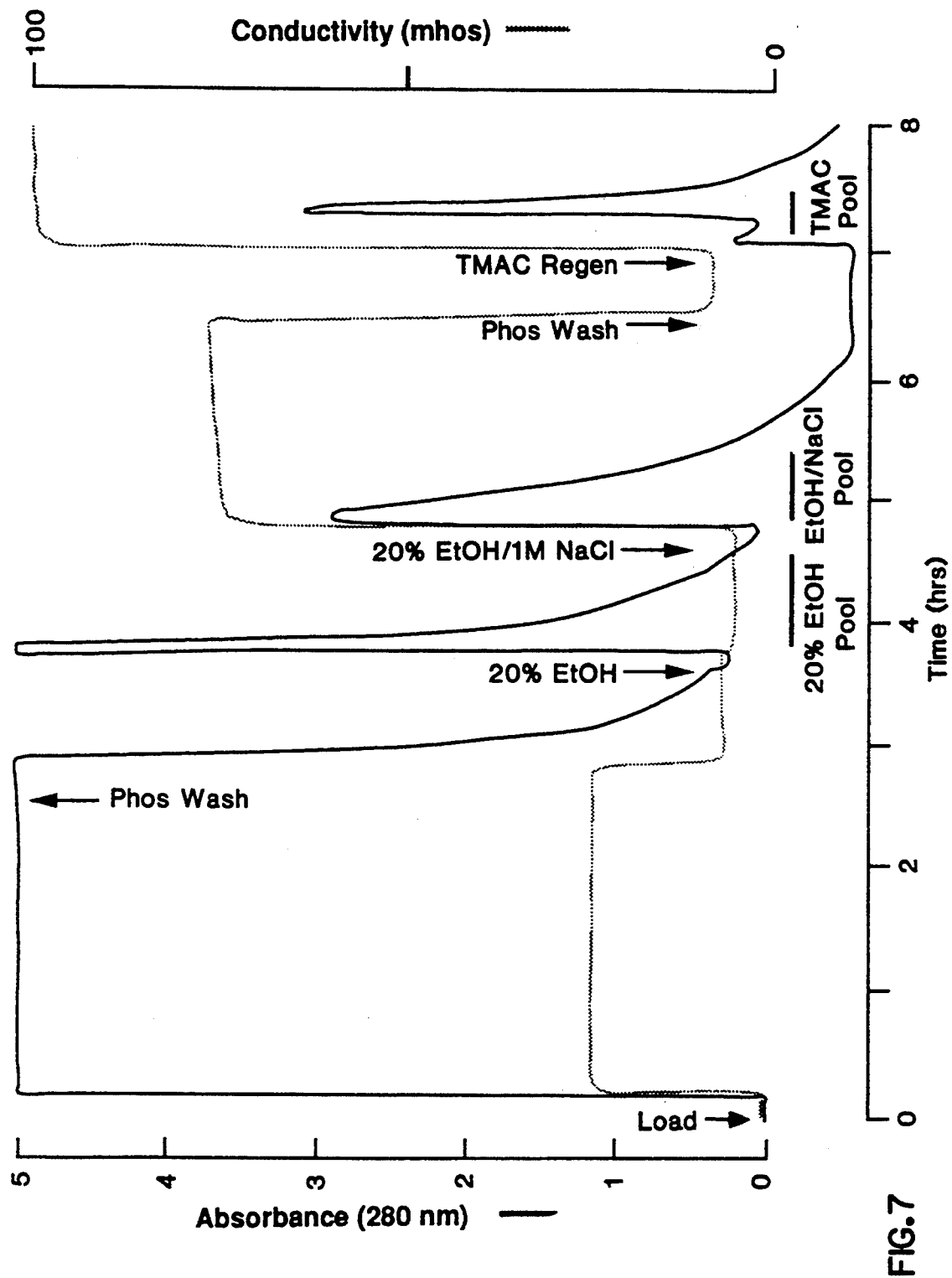
FIG. 7 shows the silica chromatogram using a 20% ethanol wash to remove impurities and a combination of ethanol and NaCl to elute bound IGF-I. The solid line is the absorbance (280 nm) and the stippled line is conductivity. Arrows indicate (from left to right): column loading, phosphate wash after loading, 20% ethanol wash, 20% ethanol and 1M NaCl wash, phosphate wash, and TMAC regeneration. Fractions were collected during elution and assayed for IGF-I by RP-HPLC assay. Fractions containing IGF-I monomer were pooled (EtOH/NaCl Pool; second horizontal line from the left between 4.7 and 5.4 hours). Other pools were made based on the chromatogram absorbance peaks and include a 20% ethanol pool (first horizontal line from the left) and a TMAC pool (third horizontal line from the left).

Two silica columns were prepared as described in Example I. Clarified fermentation broth containing approximately 20 mg of IGF-I monomer was loaded to each column. The chromatogram showing the TMAC gradient elution is shown in FIG. 6. After washing with 4 CV of 20 mM phosphate, pH 7, one column was eluted with a linear gradient of 0–1M TMAC in 20 mM phosphate, pH 7, buffer. The total gradient was 10 CV and the flow rate was approximately 5 CV/hr. At the end of the gradient, the column was washed with an additional 5 CV of 1M TMAC in buffer to ensure that no additional protein would elute. The silica chromatogram using a combination of ethanol and NaCl to elute bound IGF-I is shown in FIG. 7. After loading and washing this column as described above, the second column was eluted with 5 CV at a rate of 5 CV/hr of a 20 mM phosphate buffer containing the following:

A. 20% ethanol
B. 20% ethanol + 1.0M NaCl
C. no addition
D. 1M TMAC

The wash was included in step C to minimize the effect of ethanol and salt on the TMAC column regeneration. Approximately 5-mL fractions were collected across the elution profile for both columns and assayed for IGF-I by the RP-HPLC assay. Fractions containing IGF-I were pooled together from each column. Other pools were made based on the chromatogram from each column.

Figure 8:
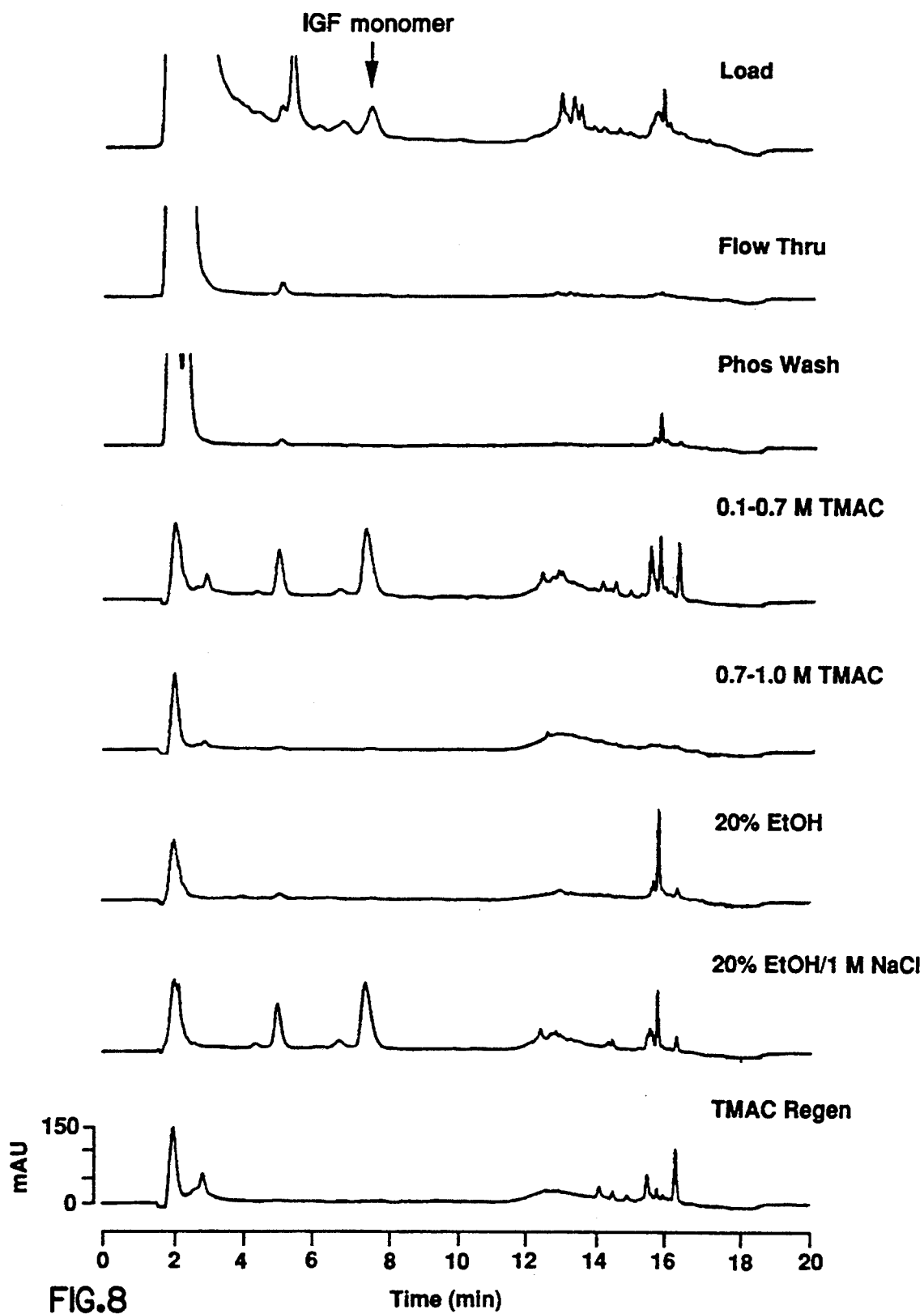
FIG. 8 shows a RP-HPLC analysis of fractions obtained from either the TMAC gradient or a combination of ethanol/NaCl to elute IGF-I from silica. The chromatograms from top to bottom in decreasing order are load, flow through, phosphate wash, 0.1–0.7M TMAC, 0.7–1.0M TMAC, 20% ethanol, 20% ethanol/1M NaCl, and TMAC regeneration. The arrow at the top chromatogram is IGF monomer.

FIG. 8 shows the RP-HPLC analysis of the pooled fractions from these columns. Samples were analyzed on a 0.46×25 cm Vydac C-18 (5μ/300Å) RP-HPLC column equilibrated with 29% acetonitrile in 0.1% TFA buffer. Protein was eluted with a linear gradient of 29–30% acetonitrile in 0.1% TFA buffer over 10 minutes, followed by a gradient of 30–40% acetonitrile over 5 minutes. The column was regenerated with 60% acetonitrile in 0.1% TFA prior to regeneration. The total time between injections was 20 minutes and a flow rate of 2 mL/min was used throughout the analysis.

In both cases, quantitative recovery of IGF-I monomer was obtained in the silica pool. However, the purity of the IGF-I pool obtained by these two methods was different. During the TMAC gradient, IGF-I eluted from approximately 0.1–0.7M TMAC. Additional TMAC did not elute any IGF-I, but did elute other proteins which were predominantly more hydrophobic than IGF-I and eluted after 11.5 min on the RP-HPLC assay (IGF-I monomer elutes at approximately 7.3 min in this assay). It is significant to note that the use of TMAC even in a gradient mode was not beneficial in specifically removing IGF-I bound to the silica.

On the other hand, a wash of 20% ethanol in phosphate buffer, pH 7, removed a significant amount of protein impurities. Following the ethanol wash, the combination of ethanol and salt was able to elute IGF-I more specifically. The ratio of IGF-I monomer to total protein was approximately 20% greater in the ethanol/NaCl pool (Table I).

TABLE I

Comparison of TMAC and EtOH/NaCl Pools by RP-HPLC or Bradford Protein Analysis

| Sample | [Protein] (mg/mL) | [IGF monomer] (mg/mL) | % IGF monomer |
|---|---|---|---|
| TMAC Pool | 2.83 | 0.42 | 14.8 |
| EtOH/NaCl Pool | 1.24 | 0.41 | 33.1 |

Figure 9:
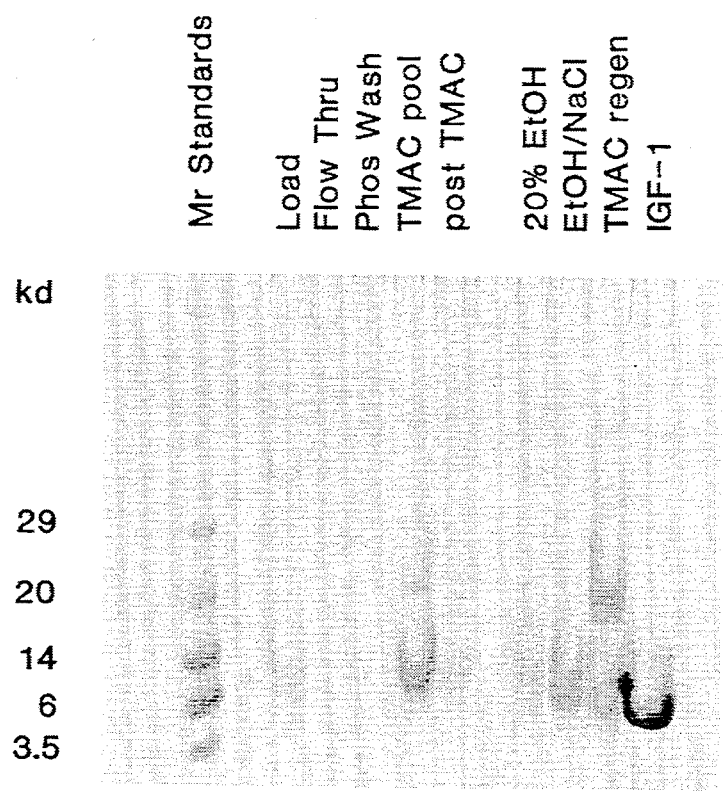
FIG. 9 shows a SDS-PAGE analysis comparing the effect of TMAC gradient with the combination of ethanol/NaCl on eluting IGF-I from silica. The lanes from left to right are molecular weight standards, load, flow through, phosphate wash, TMAC pool, post-TMAC, 20% ethanol, ethanol/NaCl, TMAC regeneration, and IGF-I.

Analysis of these samples by SDS-PAGE also demonstrates the significant improvement in purity in the ethanol/NaCl pool relative to the TMAC pool (FIG. 9). Samples (0.6 mL each) were combined with 50% trichloroacetic acid (TCA) to a final concentration of 20% TCA. After incubating on ice for 20 min, samples were spun at 10,000 ×g and the supernatant was removed. The pellet was washed two times with 0.5 mL of 95% ice-cold acetone and centrifuged, and the supernatant was removed as described above. After the pellet was air dried for approximately 5 minutes, the pellet was resuspended to the original sample volume with Laemmli sample buffer containing 1% beta-mercaptoethanol and heated for 3–5 min at 100° C. A control containing approximately 10 μg of IGF-I also was included in the TCA sample treatment. Ten μL of each sample was loaded onto a pre-casted 10–20% acrylamide gradient gel (Daiichi) and run at 30 mA for approximately 1.5 hrs using a Tris-Tricine running buffer. Schagger and Von Jagow, *Anal. Biochem.*, 166: 368 (1987). The gel was then stained with 0.1% Coomassie Brilliant Blue R-250 in 40% methanol, 10% acetic acid for approximately 1.5 hrs. Destain was performed with several changes of 40% methanol, 10% acetic acid. A reciprocating shaker was used to facilitate gel staining and desraining.

The predominant protein band in the lanes migrated with the IGF-I reference standard. However, by RP-HPLC analysis (FIG. 8) only the TMAC pool and EtOH/NaCl pool contained IGF-I monomer or misfolded IGF-I. Without being limited to any one theory, this suggests that many of the more hydrophobic proteins (which elute after 11.5 min by RP-HPLC assay) are IGF-I aggregates which, when reduced, migrate with authentic IGF-I monomer. Comparison of the TMAC pool with the EtOH/NaCl pool demonstrates the improved purity of the EtOH/NaCl pool. It is interesting to note that the TMAC regeneration of the ethanol/NaCl eluted column removed many of the proteins which were present in the TMAC gradient pool (FIGS. 8 and 9).

EXAMPLE VII

Specific Elution of IGF-I from Silica, 1000-L Scale

A. Column Preparation

One part of dry silica packing (grade 953 obtained from Davison Chemical Division of W. R. Grace) was resuspended in 5–10 parts of water (twice) to remove fines. A slurry of approximately 1 part resin to 2 parts water was transferred to an appropriately sized glass column. The bed was equilibrated with water until a constant bed length was obtained. Then the top flow adaptor was positioned above the packed bed and the column was equilibrated with water at a flow rate of approximately 20 CV/hr. Once a stable baseline was achieved, the column was ready for use. A total of 3 CV of water was generally used to prepare a uniform packed bed. A packed bed height of approximately 20 cm in a 35-cm diameter column was routinely used (approximately 20-L bed volume).

B. Sample Preparation and Loading

Approximately 1000 L of *E. coli* fermentation broth, obtained as described in Example I, was in-line heat killed at 65° C. for 30 sec. and spun through an .Alpha Lava AX centrifuge (10 LPM) to obtain a clarified supernatant, free of cell debris. The clarified broth was loaded directly onto the silica column at a rate of approximately 10 CV/hr and a total of 50 CV was loaded. During the load, most of the colored material present in the broth passed through the column as judged by visual inspection. Analysis of the column effluent by HPLC or SDS-PAGE showed that no IGF-I was lost during loading.

C. Wash and Elution

After sample loading, the column was washed with 4 CV of 20 mM phosphate, pH 7, until the absorbance (280 nm) returned to baseline. The rate for the phosphate wash and all subsequent washes was approximately 3 CV/hr. At this point, the packed bed was still a dark brown, indicating that there were appreciable amounts of fermentation components still bound to the column. Then 4 CV of 20% ethanol in 20 mM phosphate, pH 7, was applied to the column. This removed a significant amount of protein impurities relative to the small (about 5–10%) amount of IGF-I that was lost at this step. The bulk of the IGF-I that was bound to the column was preferentially eluted by a buffer containing 20% ethanol and 1M NaCl in 20 mM phosphate, pH 7.

The IGF-I elution pool was generally 4–5 CV, and 85–90% of the correctly folded IGF-I monomer was routinely recovered from the clarified fermentation broth. By SDS-PAGE, the major protein detected in the silica pool was IGF-I. The distribution of IGF-I in this pool by HPLC analysis was generally 15–25% misfolded, 2–5% oxidized, and 30–40% correctly folded monomer. The remaining portion was primarily some aggregates of IGF-I. It is significant to note that after elution, the silica column was still very dark brown. After elution of the IGF-I by the combination of ethanol and NaCl, the column was unpacked and the resin discarded after a single use.

EXAMPLE VIII

Specific Elution of Brain IGF-I from Silica

Brain IGF-I is similar to full-length IGF-I except that the brain form is missing the three N-terminal amino acids (gly-pro-glu). The host used to produce brain IGF-I was 27C7 as described in Example I. The secretion plasmid pLS33Tsc used in this example carries the brain IGF-I coding sequence. Plasmid pLS33Tsc was constructed in several steps as disclosed in detail in WO 93/11240, supra. Transformants were selected and purified on LB plates containing 20 mg/L tetracycline. This medium had the following composition: 10 g/L Bacto-Tryptone, 5 g/L yeast extract, 10 g/L sodium chloride, 20 mg/L tetracycline-HCl, and 15 g/L agar.

The fermentation process for producing brain IGF-I using *E. coli* 27C7/pLS33Tsc was performed in batches ranging from 10 to approximately 40 liters. A shake flask inoculum was prepared by inoculating 500–3000 mL of sterile LB medium containing 5 mg/L tetracycline with 1–2 mL of freshly thawed stock culture. The shake flask was incubated at 35°–39° C. at 50–200 rpm for 7–12 hours. The shake flask inoculum was used to seed a 10–50-L fermentation vessel containing production medium. The production culture was grown at 35°–39° C. with or without a temperature shift to 30° C. until the optical density at 550 nm reached 70–90.

The composition of the medium is shown below. All medium components were sterilized by heat treatment or filtration.

| Ingredient | Quantity/L |
| --- | --- |
| Glucose* | 10–300 g |
| Ammonium Sulfate | 2–6 g |
| Sodium Phosphate, Monobasic Dihydrate | 1–5 g |
| Potassium Phosphate, Dibasic | 1–5 g |
| Sodium Citrate, Dihydrate | 0.5–5 g |
| Potassium Chloride | 0.5–5 g |
| Magnesium Sulfate, heptahydrate | 0.5–5 g |
| Pluronic Polyol, L61 | 0.1–2 mL |
| Ferric Chloride, Heptahydrate | 10–100 mg |
| Zinc Sulfate, Heptahydrate | 0.1–10 mg |
| Cobalt Chloride, Hexahydrate | 0.1–10 mg |
| Sodium Molybdate, Dihydrate | 0.1–10 mg |
| Cupric Sulfate, Pentahydrate | 0.1–10 mg |
| Boric Acid | 0.1–10 mg |
| Manganese Sulfate, Monohydrate | 0.1–10 mg |
| Tetracycline | 5–30 mg |
| Yeast Extract** | 5–15 g |
| NZ Amine AS** | 5–15 g |
| Isoleucine** | 0–1 g |
| Ammonium Hydroxide | as required to control pH |
| Sulfuric Acid | as required to control pH |

*A portion of the glucose was added to the medium initially, with the remainder being fed throughout the fermentation.
**these components can be fed throughout the fermentation.

The fermentation was allowed to proceed for 35–40 hours, at which time the culture was chilled prior to harvest. The culture was inactivated by heat treatment using a continuous flow apparatus with a flow rate of 15–25 L/min at 60°–70° C. or in-tank heat inactivation (10-L scale) at 60°–70° C. for 5–15 minutes. The culture was centrifuged using a AX Alpha-laval centrifuge or equivalent and then the supernatant was clarified through a depth filter. The clarified fermentation broth was saved for further processing and the cells were discarded.

Approximately 12 L of clarified fermentation broth was loaded directly to a 500-mL silica column which was packed and equilibrated with water as described in Example I. The load rate was approximately 10 CV/hr and the column effluent at 280 nm was monitored, Throughout the loading, the effluent was greater than 20 AUFS (absorbance units full scale), indicating that most of the color in the load material did not bind to the column. After loading, the column was washed with 4 CV of 20 mM phosphate, pH 7, at a rate of 5 CV/hr and the absorbance trace returned to baseline. Hydrophobic protein impurities were removed with a 4-CV wash of 20% ethanol in 20 mM phosphate, pH 7, at a flow rate of 5 CV/hr. Fractions were analyzed by Vydac RP-HPLC analysis as described in Example VI. No brain IGF monomer was lost in any of the wash fractions. Brain IGF-I was eluted with 20% ethanol/1M NaCl in 20 mM phosphate, pH 7.

The distribution of the various forms of brain IGF-I in the 20% ethanol, 1M NaCl, 0.1M phosphate, pH 7, eluate was approximately 5–15% misfolded, 2–6% oxidized, and 30–40% correctly folded monomer. The remainder was aggregated brain IGF-I since it had the same migration pattern on SDS-PAGE under reducing conditions as brain IGF-I monomer. The recovery of brain IGF-I in the silica pool was approximately 95%.

EXAMPLE IX

Elution of an IGF-I Binding Protein from Silica

One of the IGF-I binding proteins (IGFBP-3) was purified on silica from harvested cell culture fluid. A 50-mL bed volume silica column was prepared as described in Example I. The IGFBP-3 was produced in the human kidney cell line (293s) as described in U.S. Pat. No. 5,258,287 issued Nov. 2, 1993, and Mukku et al., Insulin-like Growth Factor Binding Proteins, S. L. S. Drop and R. L. Hintz, ed,, pp. 65–70, 1989.

The serum-free culture fluid was obtained by centrifugation (4000 rpm for 10 min) and sterile filtered. Approximately 0.9 L of harvested cell culture fluid containing 18.4 mg of IGFBP-3 was loaded to the silica column (50-mL bed volume) at a rate of approximately 20 CV/hr. At the end of loading, the column was washed with approximately 4 CV of 0.1M phosphate, pH 7, until the UV trace (A280) returned to baseline. The flow rate for this and all subsequent washes was approximately 5 CV/hr.

At the end of the phosphate wash, the color of the silica column was essentially the same as it was at the start of loading. Fractions were analyzed by RP-HPLC using a Polymer Labs PLRP-S column (8 $\mu$/4000 Å). The column was equilibrated with 20% acetonitrile in 0.1% TFA. A gradient of 20–50% acetonitrile in 0.1% TFA over 9 minutes was used to elute the bound protein. Then the column was regenerated with 90% acetonitrile in 0.1% TFA before re-equilibration. The total time between injections was 13 minutes. Analysis of the flow-through and wash samples by HPLC shows that approximately 5% of the IGFBP-3 was present in these fractions. Then the column was washed with 3 CV of 20% ethanol in 0.1M phosphate, pH 7, and a small peak containing 10% of the total IGFBP-3 was obtained.

Figure 10:
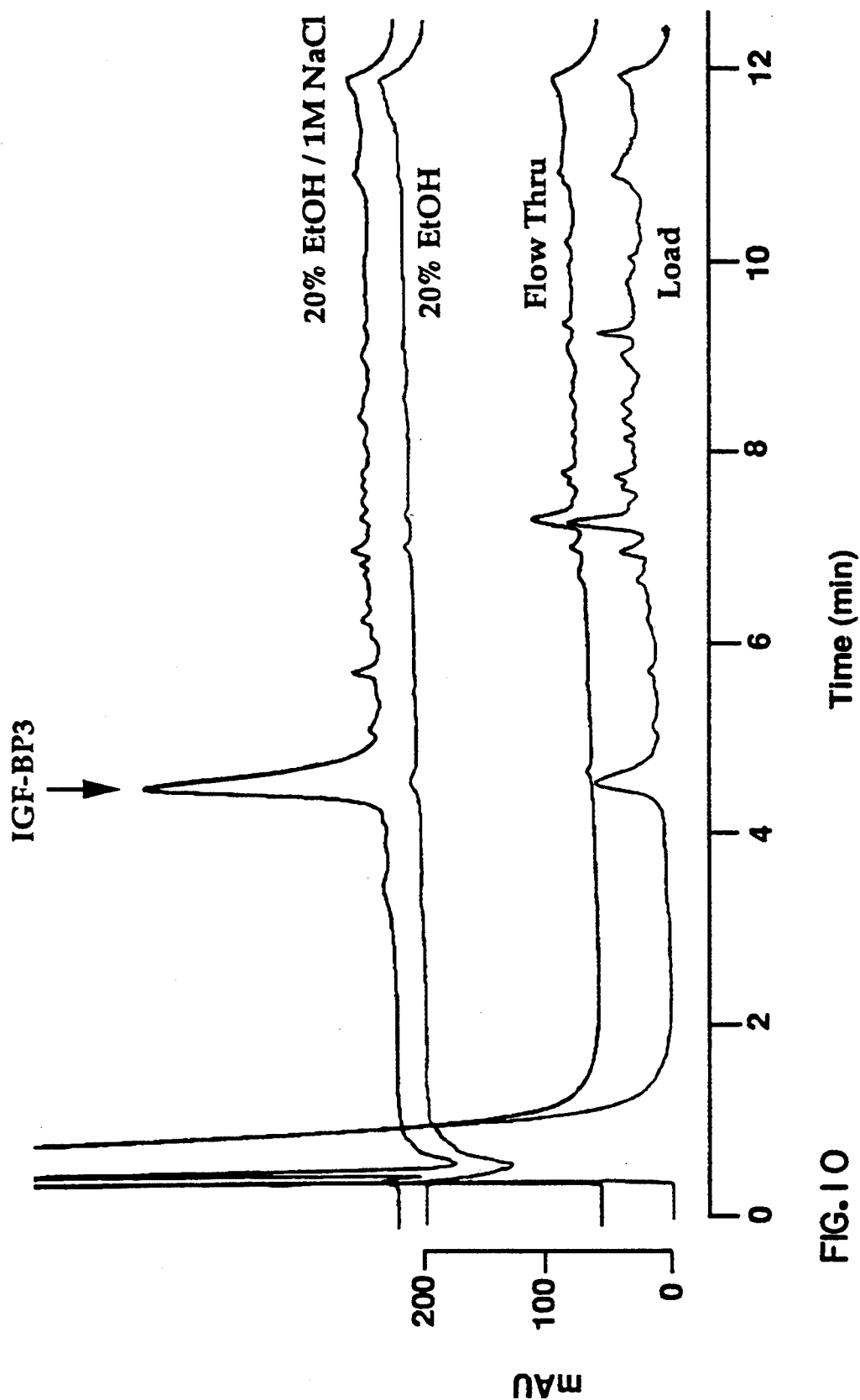
FIG. 10 shows a RP-HPLC analysis of fractions obtained from a combination of ethanol and NaCl in 20 mM phosphate, pH 7, used to elute IGF binding protein-3 (IGFBP-3) from silica. The top chromatogram is 20% ethanol/1M NaCl (with the arrow indicating IGFBP-3), the next lower chromatogram is 20% ethanol, the next lower chromatogram is flow through, and the bottom chromatogram is the load.

After a wash with 0.1M phosphate, pH 7, to remove residual ethanol, the column was washed with 3 CV of 1M NaCl in 0.1M phosphate, pH 7, and no protein was eluted. The bulk of the IGFBP-3 that was still bound to the column (13.7 mg or 75%) was eluted with 4 CV of a buffer containing a combination of 20% ethanol and 1M NaCl in 0.1M phosphate, pH 7. The purity of the 20% ethanol +1M NaCl eluate was greater than 80% IGFBP-3 (FIG. 10). After this elution, the column was regenerated with 3 CV of 2M TMAC in 0.1M phosphate, pH 7. The TMAC step removed approximately 7.5% of the IGFBP-3. The total recovery of IGFBP-3 in all of the fractions was 98%.

EXAMPLE X

Elution of VEGF from Silica

A vascular endothelial growth factor (VEGF) can also bind to silica and be eluted with a combination of ethanol and NaCl. The VEGF was produced as described in WO 90/13649 published Nov. 15, 1990 and Leung et al., Science, 246: 1306–1309 (1989), except that the cells were CHO cells rather than human embryonic kidney cells (293s). A similar vector was employed using a promoter appropriate for CHO cells as is well known in the art. After 24 hours, cells were changed into serum-free medium for an additional 48 hours. This serum-free medium was harvested by microfiltration through a 0.65 $\mu$m membrane and sterile filtered. The filtrate was applied to a 5-mL silica column packed and equilibrated with water as described in Example I. A constant flow rate of 10 CV/hr was used during the load and all subsequent wash steps.

After loading, the column was washed with 4 CV of 20 mM phosphate, pH 7, and the absorbance of the column effluent returned to the baseline. Then, the column was washed with 4 CV of 1M NaCl in 20 mM phosphate, pH 7. This removed some of the protein contaminants but did not remove any VEGF. A wash containing 4 CV of 20% ethanol in 20 mM phosphate, pH 7, was ineffective in removing any of the protein contaminants. After the 1M NaCl buffer wash, VEGF was eluted by a combination of 1.5M NaCl and 20% ethanol in 20 mM phosphate, pH 7. Approximately 90% of the VEGF which bound to the silica was removed by the combination of ethanol and NaCl. The remainder of the bound VEGF was removed with 2M TMAC in 20 mM phosphate, pH 7.

EXAMPLE XI

Elution of RANTES from Silica

Recombinant human RANTES was produced in E. coli by linking the cDNA for the full-length peptide with a bacterial STII promoter in an expression plasmid as described by Schall et al. J. Exp. Med., 177: 1821–1825 (1993). The fermentation broth was centrifuged at 4500 rpm in a Beckman RC3B centrifuge at 20° C. to remove cells. The broth was then clarified through a depth filter and loaded directly to a 500-mL silica column as described in Example I except that it was equilibrated with 4 CV of 20 mM phosphate, pH 7. A flow rate of 20 CV/hr was used to equilibrate and load the column.

After 6.6 L of clarified fermentation broth was loaded, the column was washed with 2 CV of equilibration buffer followed by 2 CV of 20% ethanol in 20 mM phosphate, pH 7, at a rate of 5 CV/hr. RANTES was eluted with a combination of 20% ethanol and 1M NaCl in 20 mM phosphate, pH 7.

EXAMPLE XII

Elution of Human MIP-i-α from Silica

Recombinant human macrophage inflammatory protein (huMIP)-1α was produced in E. coli by linking the cDNA for the full-length peptide with a bacterial STII promoter in an expression plasmid as described by Schall et al., J. Exp. Med., 177: 1821–1825 (1993). Approximately 200 mL of clarified supernatant broth was adjusted to pH 3 by the addition of 12N HCl. After stirring for 5 minutes, the pH-adjusted broth was spun for 15 min at 4000 rpm. The centrifuge supernatant was adjusted to pH 5 by the addition of NaOH.

Approximately 100 mL of this material was loaded to a 5-mL silica column packed in water as described in Example I. After loading, the column was washed with 4 CV of 10 mM citrate, pH 5. Then the column was washed with 4 CV of 10 mM citrate, 15% ethanol, pH 5, to remove impurities. The product was eluted with 10 mM citrate, 15% ethanol, 1M NaCl, pH 5. Regeneration of the silica column by 2M TMAC in 10 mM citrate, pH 5, did not remove any additional huMIP but did remove additional protein impurities.

Analytical chromatography of the different wash and elution fractions was performed at 50° C. on a Polymer Labs PLRP-S column (8 $\mu$/4000 Å). The column was equilibrated with 10% acetonitrile in 0.1% TFA. A gradient of 10–60% acetonitrile in 0.1% TFA over 9 minutes was used to elute the bound protein. Then the column was regenerated with 90% acetonitrile in 0.1% TFA before reequilibration. The total time between injections was 13 minutes. As determined by RP-HPLC, less than 5% of the total huMIP was lost in the column flow-through. The ethanol wash removed about 10% of the bound huMIP, but also removed substantial amounts of protein impurities. Approximately 85% of the bound huMIP was eluted by a combination of 15% ethanol and 1M sodium chloride. The ethanol/NaCl pool was approximately 90% pure as judged by RP-HPLC.

What is claimed is:

1. A process for selectively separating a polypeptide of interest, selected from the group consisting of IGF-I, a neurotrophin, an IGF binding protein, vascular endothelial growth factor, RANTES, and human MIP-1-alpha, from components of differing hydrophobicity in a mixture comprising the steps of:
   (a) passing the mixture through underivatized silica particles such that the polypeptide adheres to the silica particles;
   (b) washing the silica particles to remove impurities; and
   (c) eluting the polypeptide from the silica particles with a buffer comprising an alcoholic or polar aprotic solvent, excluding propylene glycol and glycerol, and an alkaline earth, an alkali metal, or an inorganic ammonium salt.

2. The process of claim 1 wherein the polypeptide is IGF-I.

3. The process of claim 2 wherein the IGF-I is full-length IGF-I.

4. The process of claim 3 wherein the silica particles have a pore size of about 225 Å.

5. The process of claim 2 wherein the IGF-I is brain IGF-I.

6. The process of claim 1 wherein the particles are washed in step (b) with an alcoholic solvent in phosphate buffer.

7. The process of claim 6 wherein the alcoholic solvent is about 20% (v/v) ethanol in pH 7 phosphate buffer.

8. The process of claim 1 wherein the buffer used in step (c) is a phosphate buffer.

9. The process of claim 1 wherein the silica particles have a pore size of about 200 to 1000 Å.

10. The process of claim 1 wherein the alkaline earth, alkali metal, or inorganic ammonium salt is a sodium, potassium, or ammonium chloride or sulfate.

11. The process of claim 10 wherein the salt is sodium chloride.

12. The process of claim 10 wherein the concentration of salt is about 0.2 to 3M.

13. The process of claim 1 wherein the solvent is methanol, ethanol, iso-propanol, n-propanol, or acetonitrile.

14. The process of claim 1 wherein the concentration of solvent is about 5-40% (v/v).

15. The process of claim 1 wherein the pH of the buffer for elution is about 5 to 8.

16. A process of purifying IGF-I from a mixture containing it comprising the steps of:
   (a) loading the mixture onto a column of underivatized silica particles;
   (b) washing the column with a buffer to remove impurities; and
   (c) eluting the IGF-I from the column using a buffer at pH of about 5-8 comprising about 5-40% (v/v) of an alcoholic or polar aprotic solvent, excluding propylene glycol and glycerol, and about 0.2 to 3M of an alkaline earth, an alkali metal, or an inorganic ammonium salt.

17. The process of claim 16 wherein the column is washed with an alcoholic solvent in phosphate buffer.

18. The process of claim 17 wherein the alcoholic solvent is about 20% (v/v) ethanol in pH 7 phosphate buffer.

19. The process of claim 16 wherein the concentration of the solvent is about 10-30% (v/v).

20. The process of claim 16 wherein the solvent is methanol, ethanol, iso-propanol, n-propanol, or acetonitrile.

21. The process of claim 16 wherein the concentration of the alkaline earth, alkali metal, or inorganic ammonium salt is about 0.5 to 2M.

22. The process of claim 21 wherein the alkaline earth, alkali metal, or inorganic ammonium salt is a sodium, potassium, or ammonium chloride or sulfate salt.

23. The process of claim 22 wherein the solvent is ethanol at a concentration of about 20% (v/v) and the salt is sodium chloride at a concentration of about 1M, in a phosphate buffer at pH 7.

24. The process of claim 16 wherein the IGF-I is full-length IGF-I.

25. The process of claim 16 wherein the IGF-I is brain IGF-I.

* * * * *